United States Patent [19]

Yamaguchi et al.

[11] Patent Number: 4,894,362

[45] Date of Patent: Jan. 16, 1990

[54] EEL GROWTH HORMONE

[75] Inventors: Kazuo Yamaguchi, Sagamihara; Akiko Saito, Machida; Susumu Sekine, Machida; Moriyuki Sato, Machida; Seiga Itoh, Sagamihara; Kunikatsu Shirahata, Komae; Tetsuya Hirano, Tokyo; Hiroshi Kawauchi, Iwate, all of Japan

[73] Assignee: Kyowa Hakko Kogyo Co., Ltd., Tokyo, Japan

[21] Appl. No.: 883,051

[22] Filed: Jul. 8, 1986

[30] Foreign Application Priority Data

Jul. 10, 1985 [JP] Japan .................................. 60-151847
Jul. 22, 1985 [JP] Japan .................................. 60-161429
Mar. 31, 1986 [JP] Japan .................................. 61-74061

[51] Int. Cl.$^4$ .......................... C07K 7/10; A61K 37/02
[52] U.S. Cl. .......................................... 514/12; 514/2; 514/21; 530/324; 530/399
[58] Field of Search .................. 530/399, 324; 514/2, 514/12, 21

[56] References Cited

FOREIGN PATENT DOCUMENTS

157423 10/1985 European Pat. Off. ..................... 7/7
166444 1/1986 European Pat. Off. ................ 12/15

OTHER PUBLICATIONS

Yamaguchi et al., Chem. Abst., 107,280(1987), Abst. No. 129332s.
Webster's Seventh New Collegiate Dictionary, G. & C. Merriam Co., Springfield, Mass., p. 263, 1969.
General and Comparative Endocrinology, vol. 30, (1976), 91:100.

Primary Examiner—Margaret Moskowitz
Assistant Examiner—F. T. Moezie
Attorney, Agent, or Firm—Fitzpatrick, Cella, Harper & Scinto

[57] ABSTRACT

According to the present invention, a fish growth hormone was isolated from an organ culture broth of the pituitary gland of eels, and further a recombinant DNA incorporated with a DNA coding for the eel growth hormone polypeptide and a microorganism containing the recombinant DNA were obtained. They can be used for mass production of an eel growth hormone.

10 Claims, 13 Drawing Sheets

EEL GROWTH HORMONE

BACKGROUND OF THE INVENTION

The present invention relates to a fish growth hormone derived from an eel and a process for producing the eel growth hormone. The present invention also pertains to a process for stimulating growth of a fish using the eel growth hormone. A growth hormone is secreted from the anterior lobe of hypophysis of vertebrates, and is a polypeptide which has a function of promoting increase in weight by adjusting a rate of incipient growth of the bone. Therefore, the present invention is expected to be of great utility in an industrial field of fish cultivation.

Mammalian growth hormones are produced in the pituitary gland. The activity and structure of the mammalian growth hormones are known. For example, human growth hormones have been reported in J. Am. Chem. Soc., 80, 4429 (1958) by U. J. Lewis, et al.; Biochem. J., 100, 754 (1966) by A. S. Hartree; and Arch. Biochem. Biophys. (Suppl.), 1, 327 (1962) by C. H. Li, et al.

As for fish growth hormones, there have been some reports on the isolation thereof, examples of which are given below.
Isolation from Tilapias
  S. W. Farmer, et al., Gen. Comp. Endocrin., 30, 91 (1976)
Isolation from Sturgeons
  S. W. Farmer, et al., Endocrinology, 108, 377 (1981)
Isolation from Carp
  A. F. Cook, et al., Gen. Comp. Endocrin., 50, 335 (1983)
Isolation from Chum salmon
  Japanese Published Unexamined Patent application No. 214798/85

On the other hand, as for mammalian growth hormone genes, rat growth hormone gene [P. H. Seeburg, et al., Nature 270, 486 (1977)], bovine and swine growth hormone genes [P. H. Seeburg, et al., DNA, 2, 37 (1983)] and human growth hormone gene [J. A. Martial, et al., Science, 205, 602 (1979)] are already known. Further, as for fish growth hormone genes, chum salmon growth hormone gene was already known by the hand of the present inventors (Japanese Published Unexamined Patent Application No. 15699/86).

However, there is no report about isolation of a growth hormone from eels, eel growth hormone genes and a process for producing an eel growth hormone polypeptide by recombinant DNA techniques using the genes.

Fish growth hormones have the effect of stimulating the growth of fish, and thus are useful as a component of baits for fish cultivation. Examples in recovery of fish growth hormone from the fish pituitary gland are known as described above, and nevertheless, it has been desired that a fish growth hormone having more excellent stimulating effect is developed. Further, the amount of the growth hormone provided by the recovery from the fish pituitary gland is limited. Therefore, it has been desired that a process for providing a large amount of fish growth hormones in a low cost is developed.

SUMMARY OF THE INVENTION

As the result of having studied to the end that a growth hormone having an excellent stimulating effect is obtained, the present inventors have found that an excellent growth hormone is obtained from an organ culture broth of the eel pituitary gland. Moreover, the present inventors have successfully recovered a DNA complementary to the eel growth hormone polypeptide and usable in the production of eel growth hormones and produced a recombinant DNA and a microorganism containing the DNA.

DESCRIPTION OF THE INVENTION

Figure 1:
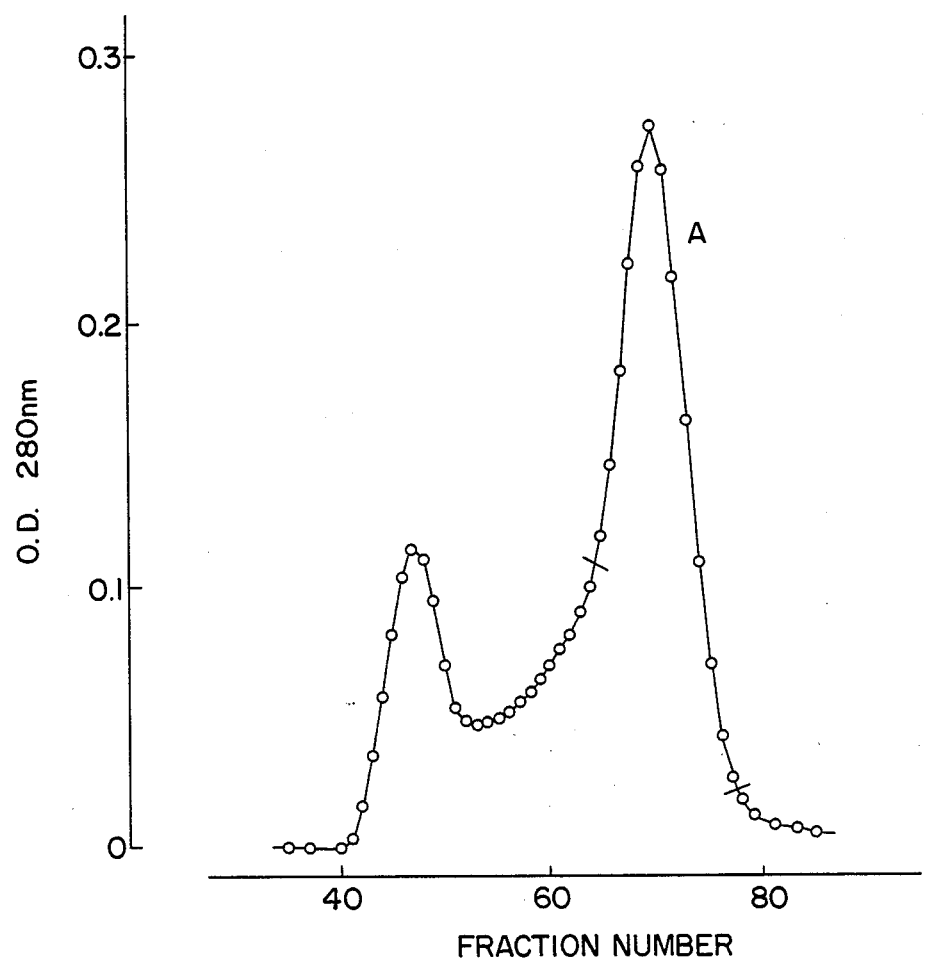
FIG. 1 illustrates the elution pattern of gel filtration of ultrafiltration concentrate of an organ culture broth of *Anguilla japonica* pituitary glands, using Sephadex G-75.

The present invention provides an eel growth hormone comprising a purified extract from an organ culture broth of the pituitary gland. The pituitary gland as used herein is obtained from heads of a fish belonging to *Actinopterygii Anguilliformes*. As the fish belonging to *Actinopterygii Angullliformes*, any species will do, and *Anguilla japonica* is mentioned as a preferred example. The pituitary glands are sterilely excised from heads cut off of *Anguilla japonica* and placed in a medium for culturing.

The culture medium is prepared by adding Eagle's MEM culture medium containing Earle's salts [H. Eagle, Science, 130, 432 (1959)], culture medium No. 199 [J. F. Morgan, et al., Proc. Soc. Exp. Biol. Med., 73, 1

(1950)]or Waymouth's MB752/1 culture medium [C. Waymouth, J. Natl. Cancer. Inst., 22, 1003 (1959)]to antibiotic such as penicillin G (80–120 U/ml, preferably 100 U/ml), streptomycin (80–120μg/ml, preferably 100 μg/ml) and fungizone (0.20–0.30 μg/ml, preferably 0.25 μg/ml), and an adequate amount of sodium bicarbonate and adjusting the mixture to at pH 7–8, preferably 7.3–7.4 and 250–300 mOsm, preferably 270–290 mOsm.

Culturing is carried out with the gas-phase full of 90–99%, preferably 95% $O_2$ and 1–10%, preferably 5% $CO_2$ at 15–20° C., preferably 18° C. for 10 weeks, while replacing the culture medium with a fresh one every seventh day.

The collected culture broths are purified by the conventional methods to be used in the polypeptide purification such as ultrafiltration, gel-filtration and chromatofocusing to recover a growth hormone polypeptide. For example, the culture broth is concentrated by using DIAFLO ultrafiltration membrane of Amicon (YM-5). The concentrate is passed through Sephadex column equilibrated with 0.01–0.05M, preferably 0.025M imidazole hydrochloride (pH 7–8, preferably pH 7.4), and eluted with the same solvent. The eluate is monitored at 280 nm by spectrophotometer, and the fractions having an absorption are collected and reconcentrated using the ultrafiltration membrane. The concentrated fractions are subjected to chromatofocusing, and passed through PBE94 (product of Pharmacia Fine Chemicals, Inc.) column equilibrated with 0.01–0.5M, preferably 0.025M imidazole hydrochloride (pH 7–8, preferably 7.4). Elution is carried out with polybuffer 74-hydrochloride (pH 4–6, preferably pH 5.0). Fractions having an absorption at 280 nm are collected, passed through Sephadex column equilibrated with 0.01–0.07M, preferably 0.05M ammonium acetate to remove the polybuffer, and eluted with the same solvent to collect the fractions having an absorption at 280 nm. The fractions are freeze-dried to obtain a growth hormone of the present invention as a white powder.

The purity of the *Anguilla japonica* growth hormone of the present invention is detected using polyacrylamide gel electrophoresis and isoelectric point electrophoresis.

The amino acid composition is analyzed by LKB 4,400 type amino acid autoanalyzer after hydrolyzing the substance at 110° C. for 22 hours in 20% constant boiling point hydrochloric acid.

An example of amino acid composition of the growth hormone of the present invention is given in Table 1.

TABLE 1

| Amino Acid | Amino Acid Composition* | |
|---|---|---|
| | A | B |
| Asp (aspartic acid) | 22.3 | 22.6 |
| Thr (threonine) | 11.2 | 11.1 |
| Ser (Serine) | 14.8 | 14.8 |
| Glu (glutamic acid) | 19.8 | 18.2 |
| Pro (proline) | 6.4 | 5.6 |
| Gly (glycine) | 11.8 | 10.9 |
| Ala (alanine) | 8.8 | 7.5 |
| Cys/2 (cysteine) | 4.2** | 4.1** |
| Val (valine) | 9.0 | 7.8 |
| Met (methionine) | 3.8 | 3.7 |
| Ile (isoleucine) | 10.0 | 9.6 |
| Leu (leucine) | 22.6 | 21.8 |
| Tyr (tyrosine) | 7.6 | 8.1 |
| Phe (phenylalanine) | 7.2 | 9.2 |
| Trp (tryptophan) | 1.0*** | 1.0*** |
| His (histidine) | 5.3 | 5.2 |
| Lys (lysine) | 14.3 | 14.8 |

TABLE 1-continued

| Amino Acid | Amino Acid Composition* | |
|---|---|---|
| | A | B |
| Arg (arginine) | 10.4 | 10.9 |

*All values are residues per mole.
**Cys was determined after oxidation by performic acid.
***Trp was determined in a form of decomposition product by methanesulfonic acid.

The analysis of amino acid sequence at the N-terminal of the growth of the growth hormone is carried out by the combination of 470A type sequencer (product of Applied Biosystem Co.) and high pressure liquid chromatography (product of Spectra Physics Co.). Further, the analysis of the whole amino acid sequence is carried out by analyzing peptide fragments into which the growth hormone is digested by cyanogen bromide and lysylendopeptidase with the above instruments.

The analyses of molecular weight, isoelectric point, etc. are carried out by the methods as shown in Example 1. The activity of growth hormone is determined by the method described in Example 11 using rainbow trouts (*Salmo irideus*). The growth hormone of the present invention stimulates growth of teleosts (Osteichthyes) such as Clupeiformes, Anguilliformes, Perciformes, Pleuronectiformes, Tetraodontiformes, etc. and thus useful in the cultivation of these fishes.

Physicochemical properties of the growth hormones GH-I and GH-II obtained in Examples of the present invention are as follows:

GH-I (i) Amino acid composition: as indicated in Column A, Table 1;
(ii) The sequence of the amino acids is as follows:

H₂N—Val—Glu—Pro—Ile—Ser—Leu—Tyr—Asn—
—Leu—Phe—Thr—Ser—Ala—Val—Asn—Arg—Ala—Gln—
—His—Leu—His—Thr—Leu—Ala—Ala—Glu—Ile—Tyr—
—Lys—Glu—Phe—Glu—Arg—Ser—Ile—Pro—Pro—Glu—
—Ala—His—Arg—Gln—Leu—Ser—Lys—Thr—Ser—Pro—
—Leu—Ala—Gly—Cys—Tyr—Ser—Asp—Ser—Ile—Pro—
—Thr—Pro—Thr—Gly—Lys—Asp—Glu—Thr—Gln—Glu—
—Lys—Ser—Asp—Gly—Tyr—Leu—Leu—Arg—Ile—Ser—
—Ser—Ala—Leu—Ile—Gln—Ser—Trp—Val—Tyr—Pro—
—Leu—Lys—Thr—Leu—Ser—Asp—Ala—Phe—Ser—Asn—
—Ser—Leu—Met—Phe—Gly—Thr—Ser—Asp—Gly—Ile—
—Phe—Asp—Lys—Leu—Glu—Asp—Leu—Asn—Lys—Gly—
—Ile—Asn—Glu—Leu—Met—Lys—Val—Val—Gly—Asp—
—Gly—Gly—Ile—Tyr—Ile—Glu—Asp—Val—Arg—Asn—
—Leu—Arg—Tyr—Glu—Asn—Phe—Asp—Val—His—Leu—
—Arg—Asn—Asp—Ala—Gly—Leu—Met—Lys—Asn—Tyr—
—Gly—Leu—Leu—Ala—Cys—Phe—Lys—Lys—Asp—Met—
—His—Lys—Val—Glu—Thr—Tyr—Leu—Lys—Val—Thr—
—Lys—Cys—Arg—Arg—Phe—Val—Glu—Ser—Asn—Cys—
—Thr—Leu—OH;

(iii) Molecular weight: about 23,000;
Isoelectric point: 6.3;
(v) Soluble in an alkaline aqueous solution and hardly soluble or insoluble in neutral and acidic aqueous solutions;
(vi) Classification as basic or acidic properties acidic polypeptide;
(vii) Color and form of substance: white powder; and
(viii) Polyacrylamide gel electrophoresis: a single band.

GH-II:

(i) Amino acid composition as indicated in Column B, Table 1;

(ii) The sequences of amino acids at the N-terminal and C-terminal are as follows:

N-terminal:

H₂N—Ile—Ser—Leu—Tyr—Asn—Leu—Phe—Thr—Ser—
—Ala—Val—Asn—Arg—Ala—Gln—His—Leu—His—Thr—
—Leu—Ala—Ala—Glu—Ile—Tyr—Lys—Glu—Phe—Glu—
—Arg—Ser—Ile—Pro—Pro—Glu—Ala—His—Arg—Gln—
—Leu—

C-terminal:

—Met—Phe—Gly—Thr—Ser—Asp—Gly—Ile—Phe—Asp—
—Lys—Leu—Glu—Asp—Leu—Asn—Lys—Gly—Ile—Asn—
—Glu—Leu—Met—Lys—Val—Val—Gly—Asp—Gly—Gly—
—Ile—Tyr—Ile—Glu—Asp—Val—Arg—Asn—Leu—Arg—
—Tyr—Glu—Asn—Phe—Asp—Val—His—Leu—Arg—Asn—
—Asp—Ala—Gly—Leu—Met—Lys—Asn—Tyr—Gly—Leu—
—Leu—Ala—Cys—Phe—Lys—Lys—Asp—Met—His—Lys—
—Val—Glu—Thr—Tyr—Leu—Lys—Val—Thr—Lys—Cys—
—Arg—Arg—Phe—Val—Glu—Ser—Asn—Cys—Thr—Leu—OH;

(iii) Molecular weight about 23,000;
(iv) Isoelectric point: 6.7;
(v) Soluble in an alkaline aqueous solution and hardly soluble or insoluble in neutral and acidic aqueous solutions;
(vi) Classification as basic or acidic properties: acidic polypeptide;
(vii) Color and form of substance white powder; and
(viii) Polyacrylamide gel electrophoresis: a single band.

The growth hormone is exemplified by GH-I and GH-II as specific embodiments of the present invention in the Examples. However, all that comprises a purified extract obtained from an organ culture broth of the pituitary gland of a fish belonging to *Actinopterygii Anguilliformes* and that has an activity of fish growth hormone, including GH-I and GH-II falls within the scope of the present invention.

Further, the present invention provides a process for producing eel growth hormone polypeptides by recombinant DNA techniques.

That is, an mRNA of fish growth hormone is isolated and used as a template to prepare a DNA (cDNA) complementary to the mRNA, and then a recombinant plasmid incorporating the cDNA is prepared. Further, the recombinant plasmid is incorporated in a host microorganism. The DNA and recombinant plasmid can be used for expression of *Anguilla japonica* growth hormone gene in bacteria such as *Escherichia coli*. Microorganisms carrying the recombinant plasmid are useful for producing a large amount of *Anguilla japonica* growth hormones in a low cost.

Furthermore, the present invention provides a DNA coding for a fish growth hormone polypeptide, a recombinant DNA incorporating the DNA and a microorganism containing the recombinant DNA.

The DNA and recombinant DNA of the present invention are prepared by the following general method.

Whole RNA is prepared from the pituitary gland of *Anguilla japonica* and passed through an oligo dT cellulose column to isolate RNA having polyadenylic acid [poly(A)RNA]. A double stranded DNA is synthesized using the poly(A)RNA as a template and a reverse transcriptase. A recombinant DNA is obtained using in vitro recombinant DNA techniques by inserting the synthesized DNA into a vector DNA such as *Escherichia coli* plasmid DNA.

A process for producing the DNA and recombinant DNA of the present invention is specifically explained below.

The pituitary gland is excised from captured *Anguilla japonica* and immediately freezed in a liquid nitrogen. Guanidium isothiocyanate is added to the freezed pituitary gland and the pituitary gland is disrupted and solubilized. Then, LiCl is added thereto, and the mixture is subjected to centrifugation to obtain whole cytoplasmic RNA as a precipitate. Alternatively, the solubilized matter with guanidium isothiocyanate is put on CsCl solution layer and subjected to ultracentrifugation to obtain an RNA as a precipitate.

The extracted RNA is dissolved in an NaCl or KCl hypertonic solution (for example 0.5M) and passed through an oligo (dT) cellulose column to allow mRNA having poly(A) to be adsorbed on the column. Elution is carried out with water or a hypotonic salt solution such as 10 mM Tris-HCl buffer to isolate the mRNA having poly(A).

Synthesis of cDNA and insertion of the cDNA into a vector are carried out according to the method of Okayama-Berg [Okayama & Berg; Mol. Cell. Biol. 2, 161 (1982)] as follows.

First, a vector primer is synthesized. A vector, e.g. pcDV1, is treated with KpnI in an adequate solution such as a solution consisting of Tris-HCl buffer (e.g. pH 7.5, 10 mM), MgCl₂ (e.g. 6 mM) and NaCl (e.g. 10 mM) to cut pcDV1 at KpnI site. The DNA is incubated with terminal deoxynacleotidyltransferase at an appropriate temperature (e.g. 37° C.) for an appropriate period (e.g. 20 minutes) in a solution consisting of Tris-HCl buffer (e.g. pH 6.8, 30 mM), sodium cacodylate (e.g. 140 mM), CoCl₂ (e.g. 1 mM), dithiothreitol (e.g. 0.1 mM) and dTTP (e.g. 0.25 mM) to add about 60 thymidyl residues to the both 3' ends of the vector DNA. Then, the DNA is cut with EcoRI in a solution consisting of Tris-HCl buffer (e.g. pH 7.5, 10 mM), MgCl₂ (e.g. 6 mM) and NaCl (e.g. 100 mM) The digested solution is fractionated by low-gelling-temperature agarose gel electrophoresis [Lars Wieslahder: Analytical Biochemistry, 98, 305 (1979), referred to as LGT method hereinafter] to recover a DNA fragment of about 3.1 Kb. Then, the DNA is dissolved in an NaCl or KCl hypertonic solution (e.g. 0.5M) and passed through a poly(dA) cellulose column to allow only vector primer molecules having poly(T) to be adsorbed on the column. Elution is carried out with water or a hypotonic salt solution such as 10 mM Tris-HCl buffer to isolate only the vector primer molecule with poly(T).

Then, a linker DNA is synthesized as follows. For example, pL1 DNA is treated with PstI in an appropriate solution such as a solution consisting of Tris-HCl buffer (e.g. pH 7.5, 10 mM), MgCl₂ (e.g. 6 mM) and NaCl (e.g. 50 mM) to cut pL1 at PstI site. The DNA is treated by the same method as in the synthesis of the vector primer except that dGTP is added in place of dTTP, and about 15 oligo dG chains are added. The DNA is cut with HindIII in an appropriate solution such as a solution consisting of Tris-HCl buffer (e.g. pH 7.5, 10 mM), MgCl₂ (e.g. 6 mM) and NaCl (e.g. 60 mM). A DNA fragment of about 0.5 Kb is fractionated by agarose gel electrophoresis and recovered with DEAE paper. Thus, a linker DNA is obtained.

The thus obtained poly(A)RNA, vector primer and linker DNA are used to synthesize cDNA as follows. The poly(A)RNA and vector primer DNA are reacted with a reverse transcriptase at an appropriate temperature (e.g. 37° C.) for an appropriate period (e.g. 40 minutes) in a solution consisting of Tris-HCl buffer (e.g. pH 8.3, 50 mM), MgCl$_2$ (e.g. 8 mM), KC1 (e.g. 30 mM), dithiothreitol (e.g. 0.3 mM), and dATP, dTTP, dCTP and dGTP (e.g. each 2 mM). About 15 oligo dC chains are added at the 3' ends of the thus obtained RNA-DNA double strand in the same conditions as in the case of the addition of dT chains to the vector primer except that dTTP is replaced with dCTP. The DNA is cut with HindIII in a solution consisting of Tris-HCl buffer (e.g. pH 7.5, 10 mM), MgCl$_2$ (e.g. 6 mM) and NaCl (e.g. 60 mM). The previously prepared linker DNA is mixed with the DNA and the mixture is incubated with *Escherichia coli* DNA ligase at an appropriate temperature (e.g. 12° C.) for an appropriate period (e.g. 16 hours) in a solution consisting of Tris-HCl buffer (e.g. pH 7.5, 20 mM), MgCl$_2$ (e.g. 4 mM), (NH$_4$)$_2$SO$_4$ (e.g. 10 mM), KCl (e.g. 0.1M) and β-nicotinamide adenine dinucleotide (β-NAD) (e.g. 0.1 mM) to prepare a ring of the cDNA and linker DNA. To the reaction solution is added 40 μM (final concentration) each of dATP, dTTP, dGTP and dCTP. *Escherichia coli* DNA ligase, *Escherichia coli* DNA polymerase I and *Escherichia coli* ribonuclease H are added to replace the RNA part with DNA and to obtain a recombinant plasmid containing a complete double stranded cDNA.

An *Escherichia coli* strain, e.g. *Escherichia coli* c600SF8 is transformed with the thus obtained recombinant plasmid, for example, by the method of Scott, et al. [Katsuya Shigesada: Saibo Kogaku (Cell Engineering), 2, 616 (1983)]. Since an ampicillin resistance gene exists in the recombinant plasmid mentioned above, the *Escherichia coli* transformant is resistant to ampicillin. Selection of a microorganism strain carrying a new recombinant plasmid DNA having a gene complementary to the mRNA of fish growth hormone from the ampicillin-resistant (Ap$^R$) strains is carried out as follows. That is, the transformants obtained above are fixed on a nitrocellulose filter and a synthetic DNA probe having a DNA sequence which is presumed from the amino acid sequence of the extracted growth hormone of *Anguilla japonica* described above is hybridized thereto to select the transformant showing strong hybridizaion [the Method of Grunstein-Hogness, Proc. Natl. Acad. Sci., USA., 72, 3961 (1975)]. The probe DNA is synthesized by a conventional triester method [J. Am. Chem. Soc., 97, 7327 (1975)]. Selection by the synthesized DNA probe is more definitely carried out by the method of Southern, et al. [J. Mol. Biol., 98, 503 (1975)]and a recombinant plasmid having the gene complementary to *Anguilla japonica* growth hormone mRNA is identified by the same method mentioned above.

pEGH15 is an example of the thus obtained recombinant plasmids. The plasmid can be used as a source of the DNA coding for *Anguilla japonica* growth hormone.

As the *Anguilla japonica* growth hormone, GH-I and GH-II have been found and the amino acid sequences of the two growth hormones are compared with each other to find that GH-II lacks three amino acid residues from the N-terminal of GH-I. pEGH15 obtained above is a plasmid carrying the DNA coding for GH-I. Therefore, a plasmid carrying the DNA coding for GH-II can be prepared by recombinant DNA techniques using the DNA coding for GH-I cut out of pEGH15.

The DNA coding for *Anguilla japonica* growth hormone is cut out from the plasmid carrying the DNA and inserted into a vector DNA. The thus obtained recombinant DNA is incorporated in a microorganism and the obtained transformant is cultured to accumulate a growth hormone polypeptide of *Anguilla japonica* in a medium, which is then recovered. In this manner, the growth hormone polypeptide of *Anguilla japonica* can be produced.

As the plasmid containing the DNA coding for *Anguilla japonica* growth hormone, pEGH15 mentioned above is preferably used.

Figure 9:
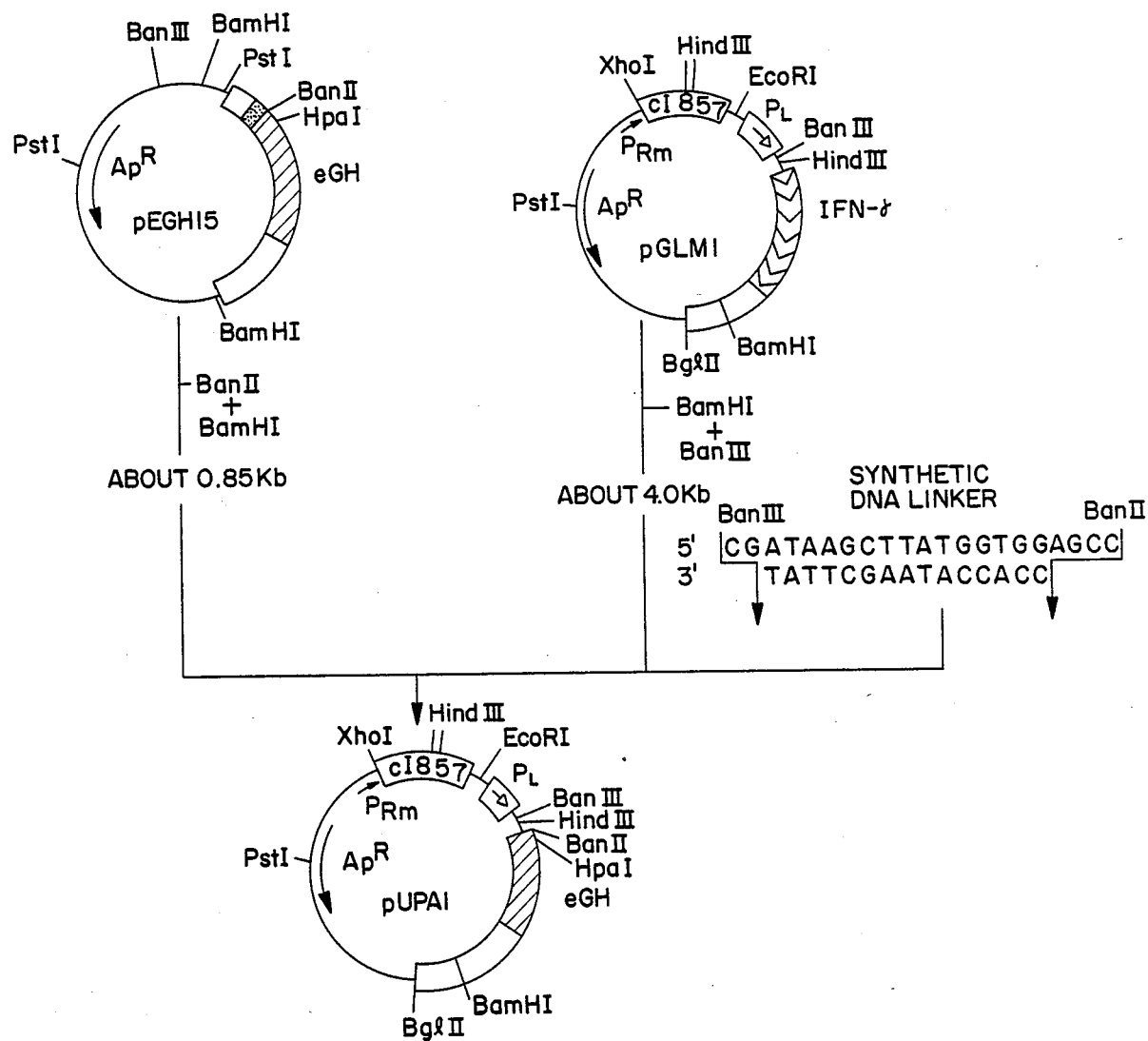
FIG. 9 illustrates the process for constructing the recombinant plasmid pUPA1.

As the vector DNA, any vector can be used so long as the DNA incorporated therein can be expressed in a microorganism. Preferably, a vector DNA wherein a DNA can be inserted downstream from a suitable promoter such as tryptophan (trp) promoter, lactose (lac) promoter and PL promoter and the length between Shine-Dalgarno sequence (referred to as SD sequence hereinafter) and initiation codon (ATG) is adjusted, for example, to 6–18 base pairs is employed. A preferred example of the vector DNA is plasmid pGLM1. pGLM1 is a plasmid as illustrated in FIG. 9 and *Escherichia coli* containing the plasmid was deposited with the Fermentation Research Institute, Agency of Industrial Science and Technology (hereinafter referred to as FRI) as *Escherichia coli* EGLM1 under FERM BP-823 on July 2, 1985. Recombination of the DNA coding for the polypeptide and the vector DNA can be carried out by a conventional recombinant DNA techniques wherein both DNAs are digested with restriction enzymes and religated with T4 DNA ligase.

In the case of pEGH15 and pGLM1 given as an example, the construction is carried out as follows. That is, BanII-BamHI digestion fragment containing the cDNA part coding for the mature growth hormone peptide of *Anguilla japonica* and the vector part is obtained from pEGH15. BamHI-BanIII digestion fragment containing P$_L$ promoter and cI857 gene is obtained from pGLM1. On the other hand, the synthetic DNA linker as shown below is prepared.

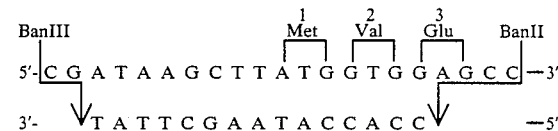

The both DNA fragments and synthetic DNA linker described above are ligated with T4 DNA ligase to obtain the recombinant plasmid pUPA1 illustrated in FIG. 9. The plasmid has a construction wherein a region coding for mature growth hormone of *Anguilla japonica* (GH-I) is ligated downstream from the PL promoter.

Reaction conditions required for the recombinant techniques described above are generally as follows.

Digestion of the DNA with restriction enzymes is usually carried out by reacting 0.1 20 μg of the DNA with 0.1–100 units, preferably 1–3 units of the restriction enzyme per 1 μg of the DNA in a mixture of 2–200 mM, preferably 10–40 mM Tris-HCl (pH 6.0–9.5, preferably pH 7.0–8.0), 0–200 mM NaCl and 2–30 mM, preferably 5–10 mM MgCl$_2$ at 20°–70° C. (optimum temperature depends on the restriction enzymes used) for 15 minutes to 24 hours.

Reaction is usually stopped by heating at 55°–75° C. for 5–30 minutes, or alternatively by inactivating the restriction enzyme with a reagent such as phenol or diethylpyrocarbonate.

Purification of the DNA fragments formed by digestion with restriction enzymes is carried out by LGT method or polyacrylamide gel electrophoresis.

Ligation of the DNA fragments is carried out with 0.3–10 units of T4 DNA ligase in a mixture of 2–200 mM, preferably 10–40 mM Tris-HCl (pH 6.1–9.5, preferably 7.0–8.0), 2–20 mM, preferably 5–10 mM MgCl$_2$, 0.1–10 mM preferably 0.5–2.0 mM ATP and 1–50 mM, preferably 5–10 mM dithiothreitol at 1°–37° C., preferably 3°–20° C. for 15 minutes to 72 hours, preferably 2–20 hours.

The recombinant plasmid DNA formed by the ligation reaction is introduced into *Escherichia coli* by the transformation method of Cohen, et al. [S. N. Cohen, et al.: Proc. Natl. Acad. Sci. USA, 69, 2110 (1972)], if necessary.

Isolation of the recombinant plasmid DNA from *Escherichia coli* carrying the DNA is carried out by cesium chloride-ethidium bromide density-gradient ultracentrifugation method [D.B. Clewell, et al.: Proc. Natl. Acad. Sci., USA, 62, 1159 (1969)]or the method of Birnboim, et al. [H. C. Birnboim, et al.: Nucleic Acids Res. 7, 1513 (1979)].

Plasmid DNA is digested with 1–10 kinds of restriction endonucleases and the cleavage sites are examined by agarose gel electro-phoresis or polyacrylamide gel electrophoresis. Further, if necessary, the base sequence of the DNA is determined by the method of Maxam-Gilbert [Proc. Natl. Acad. Sci. 74, 560 (1977)]or the method of Sanger [Sanger, et al.: Proc. Natl. Acad. Sci. USA, 74, 5463 (1977); Amersham Co., M13 cloning and sequencing handbook]using M13 phage.

The growth hormone polypeptide of *Anguilla japonica* of the present invention is produced by the following method.

That is, *Escherichia coli* K-12 C600 [R. K. Appleyard, Genetics, 39, 440 (1954)]is transformed with a plasmid (e.g. pUPA1) and an *Escherichia coli* strain carrying pUPA1 is selected from the ampicillin resistant colonies. The *Escherichia coli* strain carrying pUPA1 is cultured in a medium to produce the growth hormone polypeptide of *Anguilla japonica* in the cultured product.

As the medium to be used herein, either a synthetic medium or a natural medium can be used so long as it is suitable for the growth of *Escherichia coli* and the production of the growth hormone polypeptide of *Anguilla japonica*.

As the carbon source, glucose, fructose, lactose, glycerol, mannitol, sorbitol, etc. may be used. As the nitrogen source, NH$_4$Cl, (NH$_4$)$_2$SO$_4$, casamino acid, yeast extract, polypeptone, meat extract, Bacto-Tryptone, corn steep liquor, etc. may be used. In addition, nutrients such as K$_2$HPO$_4$, KH$_2$PO$_4$, NaCl, MgSO$_4$, vitamine B$_1$ and MgCl$_2$ may be used.

Culturing is carried out at pH 5.5–8.5 and at 18°–40° C. with aeration and stirring.

After culturing for 5–90 hours, the growth hormone polypeptide of *Anguilla japonica* is accumulated in cultured cells. The collected cells are treated with lysozyme, disrupted by repeated freezing and thawing and subjected to centrifugation. The thus obtained supernatant fluid is subjected to extraction according to a conventional method for extraction of polypeptides to recover the polypeptide.

Detection of the polypeptide is carried out by heat-dissolving the cultured cells directly in Sample buffer of Laemmli [Laemmli, Nature, 227, 680 (1970)], by subjecting the solution to SDS-polyacrylamide gel (the method of Laemmli: the reference mentioned above) and Western Blotting [Towbin, et al.: Proc. Natl. Acad. Sci., USA, 76, 4350 (1979)], and thereafter subjecting to the enzyme-antibody staining method [Kazufumi Tanabe: Saibo Kogaku (Cell Engineering), 2, 1061 (1983)]using horseradish peroxidase-labelled second antigen (product of Dako).

Certain specific embodiments of the invention are illustrated by the following representative examples.

EXAMPLE (1) Purification of *Anguilla japonica* growth hormone

The pituitary glands were sterilely excised from heads cut off of 260 individuals of *Anguilla japonica*, and put in 8 ml of a culture medium dividedly by 20 pieces.

Figure 2:
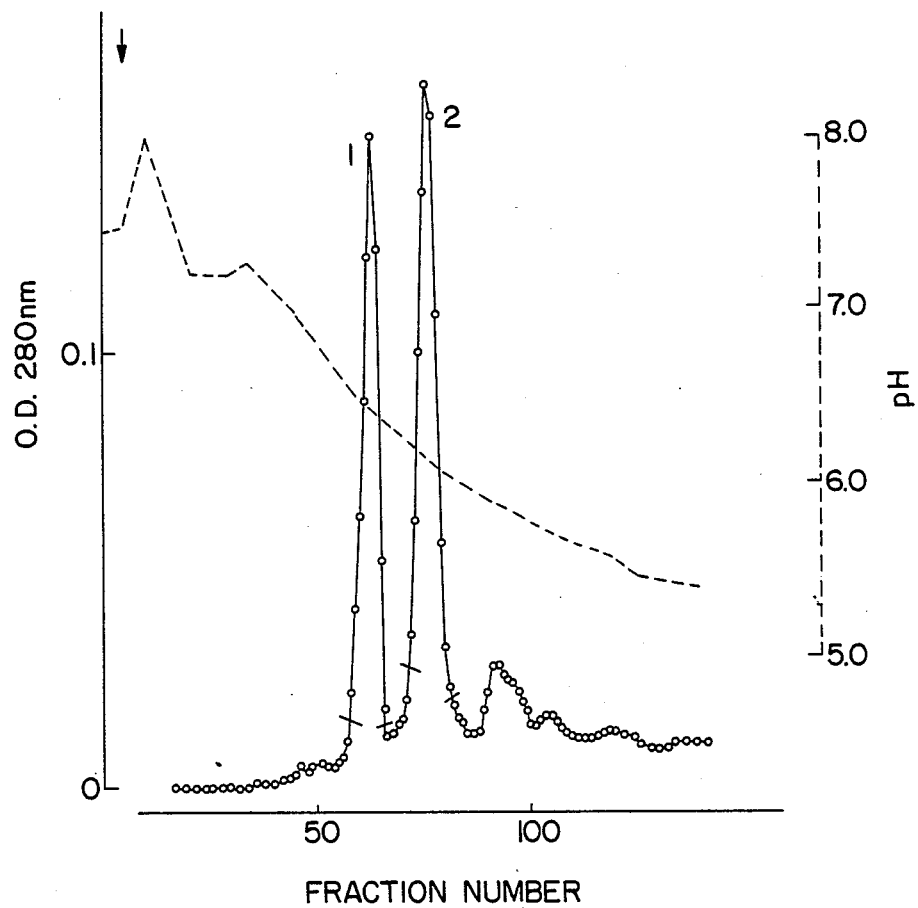
FIG. 2 illustrates fractionation of gel filtration fraction A of FIG. 1 by chromatofocusing.

The culture medium was prepared by adding Eagle's MEM culture medium containing Earle's salts [which is prepared by dissolving TC Minimum Medium Eagle, Earle, BSS, Dried (product of Difco) in a distilled water in a concentration of 9.06 g/l] to antibiotics (100 U/ml penicillin G, 100 μg/ml streptomycin and 0.25 μg/ml fungizone) and an adequate amount of sodium bicarbonate as a powder and adjusting the mixture to at pH 7.3–7.4 and the osmotic pressure of 270–290 mOsm. The pituitary glands in the culture medium were incubated in an atmosphere comprising 95% O$_2$ and 5% CO$_2$ at 18° C. The culture medium was replaced with a fresh one every seventh day, and the collected culture broths were freezed at −20° C. for storage. Under these conditions, culturing was continued for 10 weeks to obtain 750 ml of a culture broth. The culture broth was concentrated using DIAFLO ultrafiltration membrane of Amicon (YM-5) until the volume was 10.5 ml. The concentrate was passed through Sephadex G75 column (2.64×69 cm) (product of Pharmacia Fine Chemicals Inc.) equilibrated with 0.025M imidazole hydrochloride (pH 7.4), and eluted with the same solvent at a flow rate of 24.0 ml/hr. The eluate was recovered by 3 ml each of fractions, and detected at 280 nm by spectrophotometer (FIG. 1). Then, 42 ml of fractions under the peak A (Fraction Nos. 65–77) illustrated in FIG. 1 was combined and concentrated to 6 ml by the above mentioned ultrafiltration membrane. The concentrate was further fractionated by chromatofocusing. That is, the concentrate was passed through PBE94 column (1×42 cm) (product of Pharmacia Fine Chemicals, Inc.) equilibrated with 0.025M imidazole hydrochloride (pH 7.4), and eluted with polybuffer 74-hydrochloride (pH 5.0) (product of Pharmacia Fine Chemicals, Inc.) at a flow rate of 23.6 ml/hr. The eluate was fractionated in 2.9 ml each of fractions. Detection was carried out at 280 nm (FIG. 2). Fractions under peak 1 (Fraction Nos. 57–65) and those under peak 2 (Fraction Nos. 72–81) illustrated in FIG. 2 were separately combined and concentrated to 6.0 ml and 5.5 ml, respectively by the above mentioned ultrafiltration membrane. Each of the concentrates was subjected again to gel filtration to remove polybuffer. That is, the filtrate was passed through Sephadex G-75 (product of Pharmacia Fine Chemicals, Inc.) column equilibrated with 0.05M ammonium acetate (pH 8.0) and eluted with the same solvent at a flow rate of 24.0 ml/hr. The eluate was fractionated in 3.0 ml each of fractions, and the fractions having an absorption at 280 nm were combined and freeze-dried to obtain 1.35 mg of a white powder from the fractions under peak 1 and 2.00 mg of a white powder from the fractions under peak 2. The former is referred to as GH-II, the later, GH-I, hereinafter.

Figure 3:
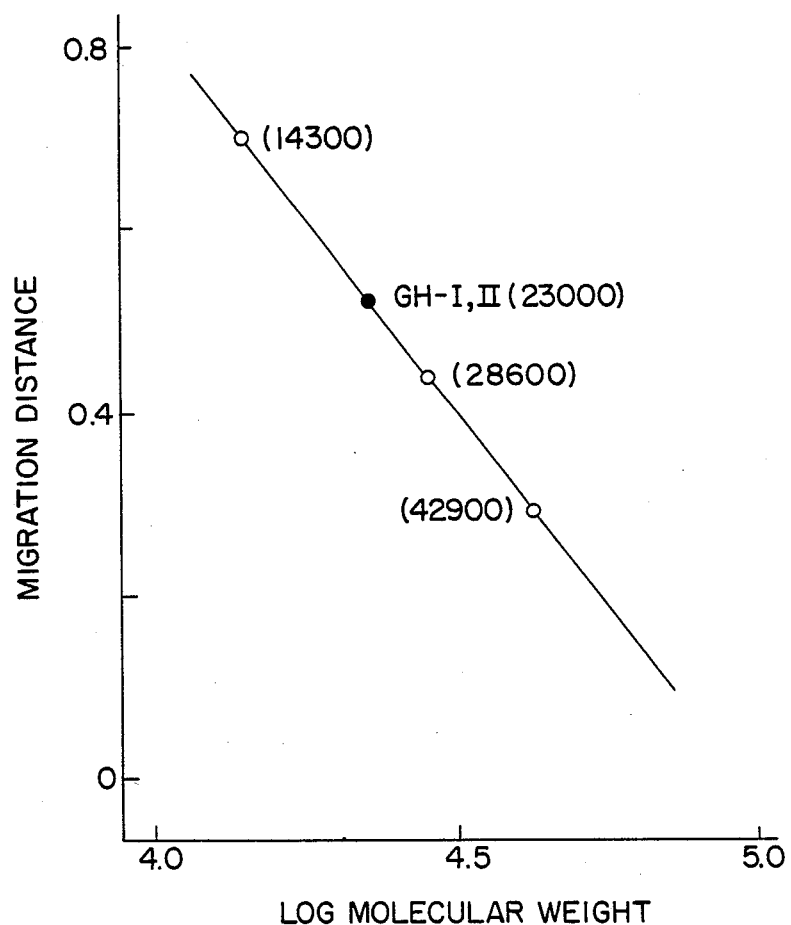
FIG. 3 is the drawing of SDS polyacrylamide gel electrophoresis whereby the molecular weight of *Anguilla japonica* growth hormone was determined according to the migration distance. Standard protein markers No. 44223 2U (product of BDH Chemical Co.) were used. Molecular weights 14.3K, 28.6K and 42.9K correspond to monomer, dimer and trimer, respectively.

(2) Determination of molecular weight:

The growth hormones mentioned above were developed on SDS (sodium lauryl sulfate) polyacrylamide gel electrophoresis (10% acrylamide/0.1% SDS). Calibration curve was obtained using standard protein markers of BDH Chemicals as standard substance (molecular weight 14.3k, 28.6k and 42.9k) and the molecular weight of either of GH-I and GH-II was calculated as about 23,000 using the calibration curve (FIG. 3). Coincidentally, either of GH-I and GH-II was detected as a single band, which shows that the hormones are nearly of 100% purity.

(3) Isoelectric point

Figure 4:
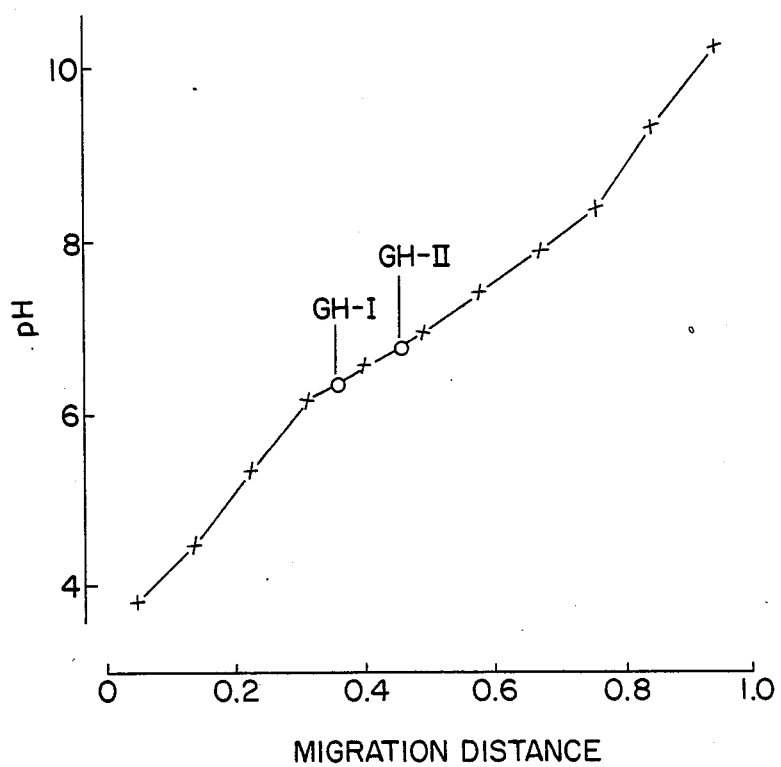
FIG. 4 is the drawing of isoelectric point electrophoresis whereby the isoelectric points of *Anguilla japonica* growth hormones are calculated.

The growth hormones GH-I and GH-II were developed on isoelectric point electrophoresis using ampholine (pH 3.5–9.5), either of which was detected as a single band. The gel was cut off and extracted with a distilled water overnight. The pH of the extracts was measured to obtain a calibration curve. The isoelectric points of GH-I and GH-II were calculated to be 6.3 and 6.7, respectively using the calibration curve (FIG. 4).

(4) Analysis of the amino acid sequences

In this step, 30 μg and 25 μg of the above-mentioned growth hormones GH-I and GH-II, respectively, obtained from *Anguilla japonica* were dissolved in 0.1% sodium lauryl sulfate aqueous solution. N-terminals were analyzed by 470A sequencer (product of Applied Biosystems) and SP8100 high pressure liquid chromatography (product of Spectra Physics) to determine the following sequences from N-terminal to the 41st (GH-I), and to 40th (GH-II) residues.

GH-I:

H$_2$N—Val—Glu—Pro—Ile—Ser—Leu—Tyr—Asn—Leu—
—Phe—Thr—Ser—Ala—Val—Asn—Arg—Ala—Gln—His—
—Leu—His—Thr—Leu—Ala—Ala—Glu—Ile—Tyr—Lys—
—Glu—Phe—Glu—Arg—Ser—Ile—Pro—Pro—Glu—Ala—
—His—Arg—

GH-II

H$_2$N—Ile—Ser—Leu—Tyr—Asn—Leu—Phe—Thr—Ser—Ala—
—Val—Asn—Arg—Ala—Gln—His—Leu—His—Thr—Leu—
—Ala—Ala—Glu—Ile—Tyr—Lys—Glu—Phe—Glu—Arg—
—Ser—Ile—Pro—Pro—Glu—Ala—His—Arg—Gln—Leu—

Figure 5:
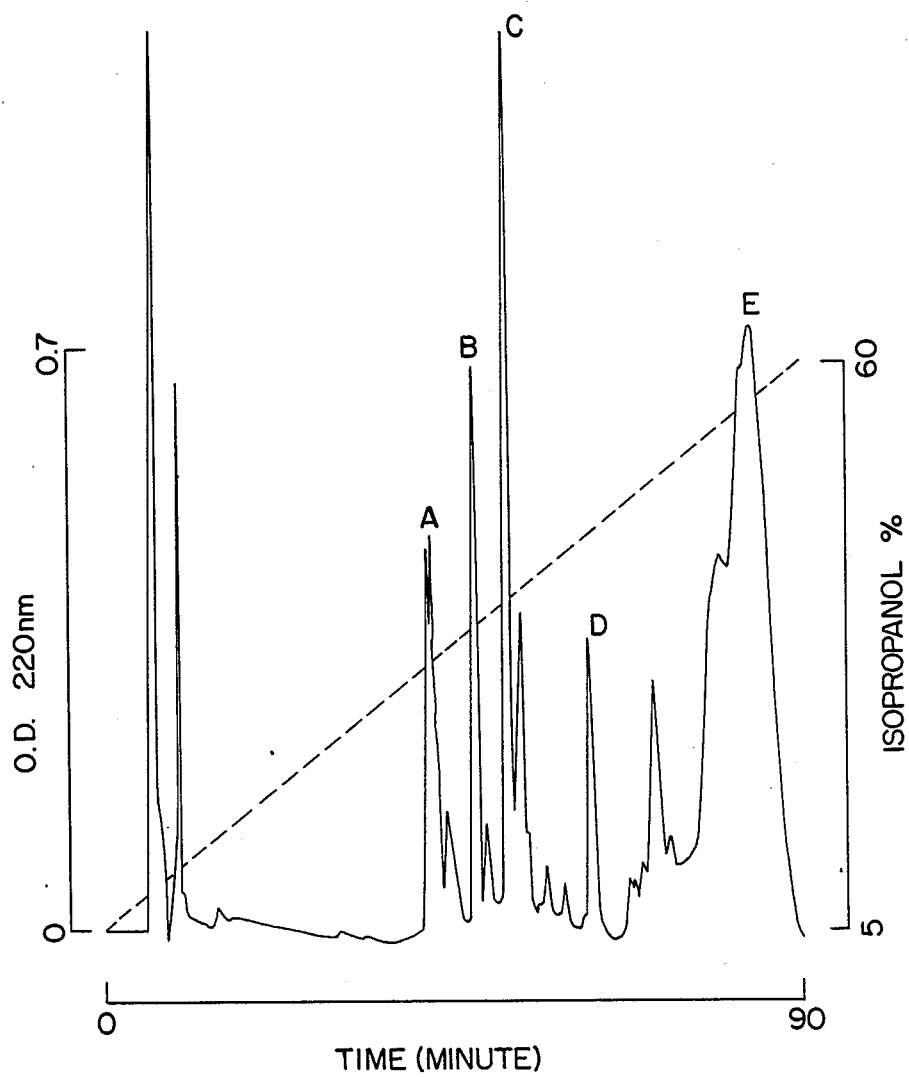
FIG. 5 illustrates separation of digestion product by cyanogen bromide of reduced carboxymethylated substance of *Anguilla japonica* growth hormone GH-I by high pressure liquid chromatography.

Then, one mg of GH-I was dissolved in one ml of a buffer (pH 8.3) comprising 0.1M Tris-HCl, 6M guanidium hydrochloride and 2 mM EDTA, and a nitrogen gas was blown through the solution for 15 minutes. To the solution was added 20 μl of mercaptoethanol and the mixture was refluxed in the dark at room temperature for 4 hours. Three mg of monoiodoacetic acid in 0.5 ml of sodium hydroxide aqueous solution was added thereto. The mixture was incubated in the dark for 15 minutes and adjusted to pH 3 with acetic acid to stop the reaction. The reaction solution was subjected to high pressure liquid chromatography by passing through TSK gel TMS250 column (0.4×5 cm, 10μm) (product of Toyo Soda Manufacturing Co., Ltd.) equilibrated with 0.1% trifluoroacetic acid aqueous solution and eluting the reaction reagent and salts out with 0.1% trifluoroacetic acid aqueous solution. Thereafter elution is carried out with a mixing solvent of isopropanol and water (90:10) containing 0.1% trifluoroacetic acid, and the eluate was freeze-dried to obtain 0.95 mg of a white powder. The powder was dissolved in one ml of 70% formic acid aqueous solution containing a 100-fold excess over methionine residues of cyanogen bromide, subjected to digestion in the dark for 18 hours, and freeze-dried. The material digested by cyanogen bromide was dissolved in 0.1 ml of 0.1% trifluoroacetic acid aqueous solution and subjected to high pressure liquid chromatography using TSK gel ODS 120T column (0.4×25 m, 5μm) (product of Toyo Soda Manufacturing Co., Ltd.) and gradient elution with 5–60% isopropanol in the presence of 0.1% trifluoroacetic acid (FIG. 5). Detection was carried out at 220 nm and a flow rate was 0.45 ml/min. The fractions under peaks A to D in FIG. 5 were analyzed by the combination of 470A type sequencer and high pressure liquid chromatography mentioned above to determine that the growth hormone has the following amino acid sequence:

Component A:
His-Lys-Val-Glu-Thr-Tyr-Leu-Lys-Val-Thr-Lys-Cys-Arg-Arg-Phe-Val-Glu-Ser-Asn-Cys-Thr-Leu-OH Component B:
Lys-Asn-Tyr-Gly-Leu-Leu-Ala-Cys-Phe-Lys-Lys-Asp Component C:
Lys-Val-Val-Gly-Asp-Gly-Gly-Ile-Tyr-Ile-Glu-Asp-Val-Arg-Asn-Leu-Arg-Tyr-Glu-Asn-Phe-Asp-Val-His-Leu-Arg-Asn-Asp-Ala-Gly-Leu Component D:
Phe-Gly-Thr-Ser-Asp-Gly-Ile-Phe-Asp-Lys-Leu-Glu-Asp-Leu Since the sequences have a homology with an Ovis growth hormone sequence [reported by C. H. Li, et al., Int. J. Peptide Protein Res., 4, 151 (1972)] and cyanogen bromide selectively cleaves the rear of Met, the sequences were aligned as -Met-D-Met-C-Met-B-Met-A and thus the sequence from the 90th to the end (C-terminal) amino acid residues was determined.

Figure 6:
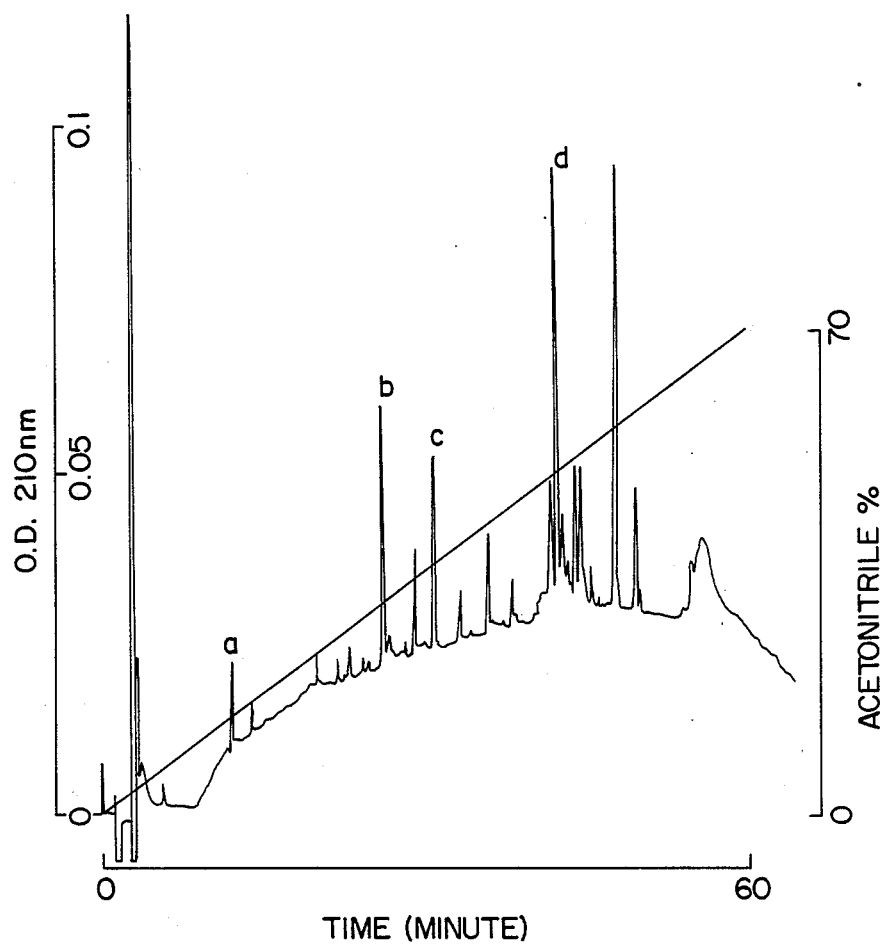
FIG. 6 illustrates separation of digestion product by lysylendopeptidase of cyanogen bromide fragment E in FIG. 5 by high pressure liquid chromatography.

The fractions under peak E had the sequence from N-terminal in GH-I. Therefore, the fractions were dissolved in 50 μl of a buffer (pH 9.1) consisting of 0.01M Tris-HCl and 4M urea, and 0.16 μg of lysylendopeptidase was added thereto. The mixture was incubated at 37° C. for 16 hours. The reaction mixture was subjected to high pressure liquid chromatography using Hipore C$_{18}$ (0.4×25 cm) (product of Bio Rad) column and gradient elution with 0–70% acetonitrile in the presence of 0.1% trifluoroacetic acid (FIG. 6). Detection was carried out at 210 nm and a flow rate was 1 ml/min. The fractions under peaks "a" to "d" were analyzed by the above-mentioned instruments to determine that the growth hormone has the following amino acid sequence:

Component a:
Asp-Glu-Thr-Gln-Glu-Lys

Component b:
Glu-Phe-Glu-Arg-Ser-Ile-Pro-Pro-Glu-Ala-His-Arg-Gln-Leu-Ser-Lys

Component c:
Thr-Leu-Ser-Asp-Ala-Phe-Ser-Asn-Ser-Leu

Component d:
Two variations of sequence were detected in Component d.

d1  Thr—Ser—Pro—Leu—Ala—Gly—Cys—Tyr—Ser—Asp—
    —Ser—Ile—Pro—Thr—Pro—Thr—Gly—Lys
d2  Ser—Asp—Gly—Tyr—Leu—Leu—Arg—Ile—Ser—Ser—
    —Ala—Leu—Ile—Gln—Ser—Trp—Val—

-continued

—Tyr—Pro—Leu—Lys.

Since the sequences have a homology with an Ovis growth hormone sequence and lysylendopeptidase selectively cleaves the rear of Lys, the sequences were aligned as b-d1-a-d2-c. Further, the sequence from N-terminal of Component b coincided with that from the 30th amino acid residue, Glu out of the sequence from N-terminal of GH-1 which had already been determined. Therefore, the sequence of 100 amino acid residues from N-terminal was determined. Further, together with the results of the digested peptides by cyanogen bromide, the whole sequence of 190 amino acid residues was determined.

As for GH-II, it was subjected to digestion by cyanogen bromide under the same conditions as GH-I. Obtained were peptide fragments corresponding to four peptides at the C-terminal end of GH-I, the sequences of which utterly coincided with those of GH-I. Accordingly, it was proved that the sequence of 90 amino acid residues at the C-terminal end is the same as GH-I.

EXAMPLE 2

Preparation of poly(A)RNA from the pituitary gland of *Anguilla japonica*

An RNA having poly(A) was prepared from the pituitary gland of *Anguilla japonica* according to guanidium thiocyanate-lithium chloride method [Cathala et al., DNA, 2, 329 (1983)]in the following manner.

First, 0.5g of the freezed pituitary gland of *Anguilla japonica* (corresponding to about 1,000 individuals) was disrupted and solubilized with Teflon homogenizer (5 rpm) in 10 ml of a solution consisting of 5M guanidium thiocyanate, 10 mM EDTA, 50 mM Tris-HCl (pH 7) and 8% (V/V) β-mercaptoethanol. The solubilized matter was put in a centrifuge tube, and 70 ml of 4M LiCl solution was added. The mixture was stirred and incubated at 4° C. for 20 hours. Centrifugation was carried out at 9,000 rpm for 90 minutes using Hitachi RPR10 rotor (Hitachi, Ltd.) to recover RNAs as a precipitate. The RNA precipitate was suspended in 100 ml of a solution consisting of 4M urea and 2M lithium chloride, and centrifuged at 9,000 rpm for 60 minutes using Hitachi RPR10 rotor to recover RNAs as a precipitate again. The RNA precipitate was dissolved in 10 ml of a solution consisting of 0.1% sodium lauryl sulfate, 1 mM EDTA and 10 mM Tris-HCl (pH 7.5), extracted with phenol-chloroform and treated with ethanol to obtain purified RNA as a precipitate.

About 1 mg of the thus obtained RNA was dissolved in 1 ml of a solution consisting of 10 mM Tris-HCl (pH 8.0) and 1 mM EDTA. The solution was incubated at 65° C. for 5 minutes and 0.1 ml of 5M NaCl was added. The mixture was subjected to oligo(dT) cellulose column (product of P-L Biochemicals, column volume 0.5 ml) chromatography. The mRNA having poly(A) adsorbed on the column was eluted with a solution consisting of 10 mM Tris-HCl (pH 7.5) and 1 mM EDTA to obtain about 7 μg of the mRNA having poly(A).

EXAMPLE 3

Figure 7I:
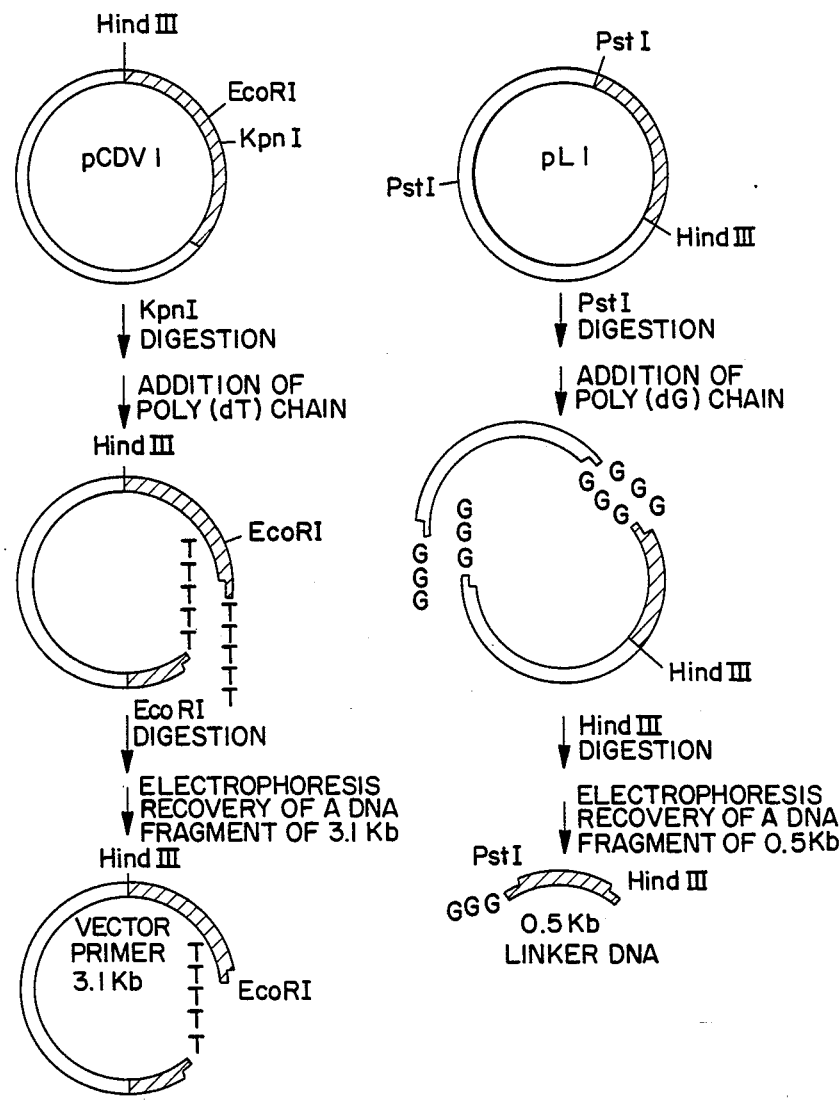
FIG. 7 consisting of part (1) and part (2) is a flow sheet for synthesizing cDNA by the method of Okayama-Berg and constructing a recombinant plasmid containing the DNA.
Figure 7:
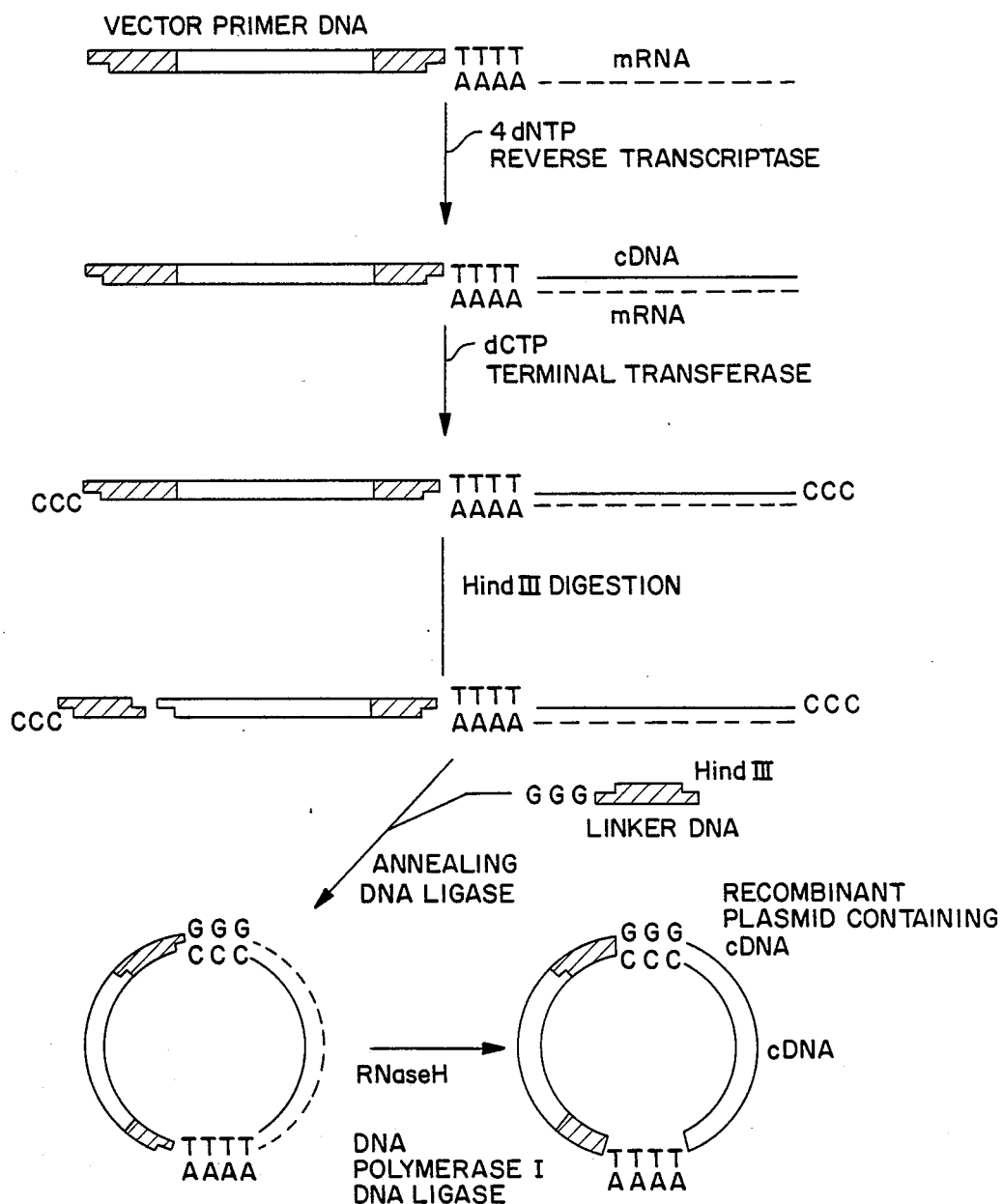

Synthesis of a cDNA and insertion of the cDNA into a vector:

Synthesis of a cDNA and construction of a recombinant plasmid carrying the cDNA were carried cut out according to the method of Okayama-Berg [Mol. Cell. Biol., 2, 161 (1982)]in the following manner. The process is outlined in FIG. 7.

First, 400 μg of pcDV1 [Okayama Berg: Mol. Cell. Biol., 3, 280 (1983)]was added to 300 μl of a solution consisting of 10 mM Tris-HCl (pH 7.5), 6 mM MgCl$_2$ and 10 mM NaCl, and further 500 units of KpnI (product of Takara Shuzo Co., the restriction enzymes used hereinafter are all products of Takara Shuzo Co., unless otherwise specified) was added. Reaction was carried out at 37° C. for 6 hours to cut the plasmid at KpnI site. After phenol-chloroform extraction, a DNA was recovered by ethanol precipitation. About 200 μg of the DNA cut with KpnI was added to 200 μl of a solution prepared by adding 0.25 mM dTTP to a buffer (referred to as TdT buffer hereinafter) consisting of 40 mM sodium cacodylate, 30 mM Tris-HCl (pH 6.8), 1 mM CaCl$_2$ and 0.1 mM dithiothreitol (referred to as DTT hereinafter). Further, 81 units of terminal deoxynucleotidyl transferase (referred to as TdT hereinafter) (product of P-L Biochemicals) was added and reaction was carried out at 37° C. for 11 minutes, whereby poly(dT) chains (about 67 mer) were added to the 3' ends of pcDV1 cleaved with KpnI. About 100 μg of pcDV1 DNA associated with poly(dT) chains was recovered from the solution by phenol-chloroform extraction and ethanol precipitation. The DNA was added to 150 μl of a buffer consisting of 10 mM Tris-HCl (pH 7.5), 6 mM MgCl$_2$ and 100 mM NaCl. Further, 360 units of EcoRI was added and reaction was carried out at 37° C. for 2 hours. The reaction product was subjected to LGT method to obtain a DNA fragment of about 3.1 Kb which is about 60 μg of pcDV1 with poly(dT) chains. The DNA was dissolved in 500 μl of a solution consisting of 10 mM Tris-HCl (pH 8.0) and 1 mM EDTA. The solution was incubated at 65° C. for 5 minutes and 50 μl of 5M NaCl was added under ice cooling. The mixture was subjected to oligo(dA) cellulose column (product of Collaborative Research) chromatography. The DNA with enough poly(dT) chains was adsorbed on the column. Elution was carried out with a solution consisting of 10 mM Tris-HCl (pH 8.0) and 1 mM EDTA to obtain 27 μg of pcDV1 with poly(dT) chains (referred to as vector primer hereinafter).

Then, a linker DNA was prepared in the following manner.

About 14 μg of pL1 [Okayama & Berg: Mol. Cell. Biol., 3, 280 (1983)]was added to 200 μl of a buffer consisting of 10 mM Tris-HCl (pH 7.5), 6 mM MgCl$_2$ and 50 mM NaCl. Further, 50 units of PstI was added and reaction was carried out at 37° C. for 4 hours to cut pL1 DNA at PstI site. The reaction product was subjected to phenol-chloroform extraction and ethanol precipitation to recover about 13 μg of pL1 DNA cleaved with PstI. About 13 μg of the DNA was added to 50 of TdT buffer containing 0.25 mM (final concentration) dGTP. Further, 54 units of TdT (product of P-L Biochemicals) was added and incubation was carried out at 37° C. for 13 minutes to add (dG) chains (about 14 mer) to the 3' ends of pL1 cut with PstI. A DNA was recovered by phenolchloroform extraction and ethanol precipitation. The DNA was added to 100 μl of a buffer consisting of 10 mM Tris-HCl (pH 7.5), 6 mM MgCl$_2$ and 60 mM NaCl. Further, 80 units of HindIII was added and incubation was carried out at 37° C. for 3 hours to cut pL1 DNA at HindIII site. The reaction product was fractionated by agarose gel electrophoresis and a DNA fragment of about 0.5 Kb was recovered by DEAE paper method [Dretzen, et al., Anal. Biochem., 112, 295 (1981)]. The DNA was linker DNA with oligo(dG) chain (referred to as linker-DNA hereinafter).

About 2 μg of the poly(A)RNA and about 1.4 μg of the vector primer prepared above were dissolved in 22.3 μl of a solution consisting of 50 mM Tris-HCl (pH 8.3), 8 mM MgCl$_2$, 30 mM KCl, 0.3 mM DTT, 2 mM dNTP (dATP, dTTP, dGTP and dCTP) and 10 units of ribonuclease inhibitor (product of P-L Biochemicals). Ten units of reverse transcriptase (product of Seikagaku Kogyo Co.) was added and incubation was carried out at 37° C. for 40 minutes to synthesize a DNA complementary to the mRNA. The reaction product was subjected to phenolchloroform extraction and ethanol precipitation to recover a vector-primer DNA associated with RNA-DNA double stranded chain. The DNA was dissolved in 20 μl of TdT buffer containing 66 μM dCTP and 0.2 μg of poly(A). Fourteen units of TdT (product of P-L Biochemicals) was added and incubation was carried out at 37° C. for 8 minutes to add (dC) chains (12 mer) to the 3' ends of the cDNA. The reaction product was subjected to phenol-chloroform extraction and ethanol precipitation to recover a cDNA-vector primer DNA associated with (dC) chains. The DNA was dissolved in 400 μl of a solution consisting of 10 mM Tris-HCl (pH 7.5), 6 mM MgCl$_2$ and 60 mM NaCl. Twenty units of HindIII was added and incubation was carried out at 37° C. for 2 hours to cut the DNA at HindIII site. The reaction product was subjected to -phenol-chloroform extraction and ethanol precipitation to obtain 0.5 pmole of a cDNA-vector primer DNA associated with (dC) chains. Then, 0.08 pmole of the DNA and 0.16 pmole of the linker-DNA mentioned above were dissolved in 40 μl of a solution consisting of 10 mM Tris-HCl (pH 7.5), 0.1M NaCl and 1 mM EDTA and incubations were carried out at 65° C., 42° C. and 0° C. for 10 minutes, 25 minutes and 30 minutes, respectively. The reaction solution was adjusted to 400 μl (total volume) of a solution having a composition of 20 mM Tris-HCl (pH 7.5), 4 mM MgCL$_2$, 10 mM (NH$_4$)$_2$SO$_4$, 0.1 KCl and 0.1 mM β-NAD. Ten units of *Escherichia coli* DNA ligase (product of New England Biolabs) was added to the reaction solution and incubation was carried out at 11° C. overnight. The reaction solution was adjusted to a solution containing 40 μM dNTP and 0.15 mM β-NAD. Five units of *Escherichia coli* DNA ligase, 7 units of *Escherichia coli* DNA polymerase I (product of P-L Biochemicals) and 2 units of *Escherichia coli* ribonuclease H (product of P-L Biochemicals) were added and incubation was carried out at 12° C. for one hour and successively at 25° C. for one hour. By the reaction mentioned above, a recombinant DNA containing the cDNA was cyclized, the RNA part of the RNA-DNA double stranded chain was replaced with the DNA and a recombinant plasmid having complete double stranded DNA was formed.

EXAMPLE 4

Selection of a recombinant DNA containing *Anguilla japonica* growth hormone cDNA:

*Escherichia coli* c600SF8 strain [Cameron: Proc. Natl. Acad. Sci. USA, 72, 3416 (1975), the strain was deposited with FRI under FERM BP-1070 on May 27, 1986] was transformed using the recombinant plasmid obtained in Example 3 by the method of Scott, et al. [Katsuya Shigesada: Saibo Kogaku (Cell Engineering) 2, 616 (1983)]. About 2,400 colonies thus obtained were fixed on nitrocellulose. Three strains were selected which hybridized strongly at 38° C. with the probe wherein a synthetic DNA corresponding to the 27th to 32nd amino acid sequence from the N-terminal of the *Anguilla japonica* growth hormone, i.e.

```
3'                                              5'
 1  2  3  4  5  6  7  8  9 10 11 12 13 14 15 16 17
 T  A  A  A  T  A  T  T  T  C  T  T  A  A  A  C  T   17 mer
      (T)      (G)    (C)    (C)    (G)
      (G)
```

(the 3rd base is one of A, T and G, the 6th is A or G, the 9th is T or C, the 12th is T or C, 15th is A or G and combination. of the bases makes 48 kinds of synthetic DNAs) was-labelled with $^{32}$P [the method of Grunstein-Hogness, Proc. Natl. Acad. Sci., USA, 72, 3961 (1975)]. It was confirmed by the method of Southern [J. Mol. Biol., 98, 503 (1975)] that the 3 strains hybridized with the probe mentioned above and a synthetic DNA probe corresponding to the amino acid sequence around the C-terminal, i.e.

```
5'                                  3'
 1  2  3  4  5  6  7  8  9 10 11 12 13 14
 C  A  T  A  A  A  G  T  A  G  A  A  A  C   14 mer
     (C)    (G)    (T)    (G)
                          (G)
                          (C)
```

(the 3rd base is T or C, the 6th is A or G, the 9th is one of A, T, G and C, the 12th is A or G and combination of the bases makes 32 kinds of synthetic DNAs). The plasmids named pEGH8, 9 and 15 respectively have the DNA sequence presumed from the amino acid sequence of the *Anguilla japonica* growth hormone and are considered to contain *Anguilla japonica* growth hormone cDNA.

EXAMPLE 5

Figure 8:
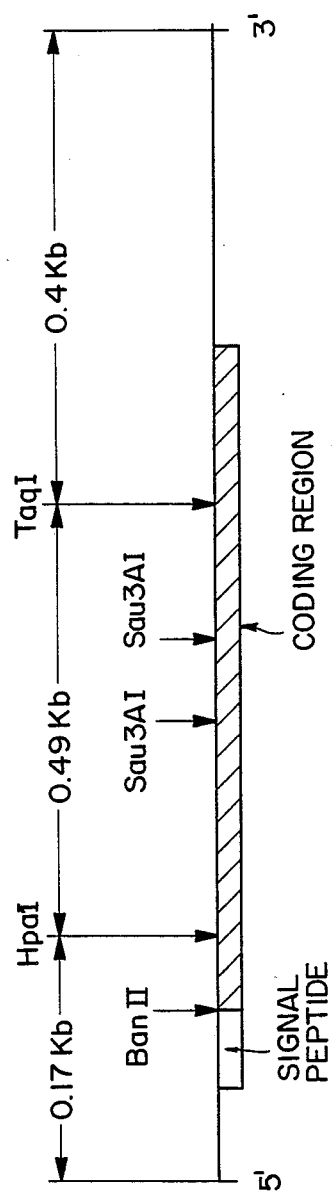
FIG. 8 illustrates the restriction enzyme map of the cDNA coding for *Anguilla japonica* growth hormone in pEGH15.

The base sequence of plasmid pEGH15:

The three plasmids obtained above were digested with various restriction endonucleases and cleavage maps of the cDNA parts were determined. The restriction endonuclease map of the cDNA in plasmid pEGH15 is illustrated in FIG. 8.

Then, pEGH15 which hybridizes strongly with the synthetic DNA probe described in Example 4 and which is considered to contain the cDNA having an almost complete length was examined by the method of Sanger using M13 phage [Sanger, et al.; Proc. Natl. Acad. Sci., USA, 74, 5463 (1977): Amersham, M13 cloning and sequencing handbook] to determine the whole nucleotide sequence of the translational region. The nucleotide sequence is illustrated in Table 2. In Table 2, the base numbers 1–57 code for signal peptide and 58–627 code for the mature peptide of *Anguilla japonica* growth hormone. It was confirmed that the amino acid sequence from the cDNA sequence in pEGH15 utterly coincides with a part of the amino acid sequence determined from the natural *Anguilla japonica* growth hormone and that the cDNA codes for *Anguilla japonica* growth hormone (GH-I).

TABLE 2

```
        10         20         30         40         50         60
ATGGCATCAGGGTTCCTTCTGTGGCCGGTCTTACTGGTCAGCTTCTCTGTGAACGCGGTG
Met Ala Ser Gly Phe Leu Leu Trp Pro Val Leu Leu Val Ser Phe Ser Val Asn Ala Val 70         80         90        100        110        120
GAGCCCATTTCCCTCTACAACCTCTTCACCAGCGCTGTTAACCGAGCACAGCACCTGCAC
Glu Pro Ile Ser Leu Tyr Asn Leu Phe Thr Ser Ala Val Asn Arg Ala Gln His Leu His 130        140        150        160        170        180
ACACTGGCTGCCGAAATATACAAGGAATTTGAGCGAAGCATCCCACCCGAGGCCCACAGA
Thr Leu Ala Ala Glu Ile Tyr Lys Glu Phe Glu Arg Ser Ile Pro Pro Glu Ala His Arg 190        200        210        220        230        240
CAGCTCAGCAAGACCTCCCCATTGGCCGGCTGTTACTCCGACTCCATCCCTACCCCCACA
Gln Leu Ser Lys Thr Ser Pro Leu Ala Gly Cys Tyr Ser Asp Ser Ile Pro Thr Pro Thr 250        260        270        280        290        300
GGCAAAGATGAAACGCAGGAGAAATCGGATGGGTACTTGCTGCGCATCTCCTCAGCCCTG
Gly Lys Asp Glu Thr Gln Glu Lys Ser Asp Gly Tyr Leu Leu Arg Ile Ser Ser Ala Leu 310        320        330        340        350        360
ATCCAGTCATGGGTGTATCCTCTGAAGACCCTGAGCGATGCTTTCACTAACAGCCTGATG
Ile Gln Ser Trp Val Tyr Pro Leu Lys Thr Leu Ser Asp Ala Phe Ser Asn Ser Leu Met 370        380        390        400        410        420
TTTGGGACCTCTGATGGGATCTTTGATAAGCTGGAGGACCTGAACAAGGGCATCAATGAA
Phe Gly Thr Ser Asp Gly Ile Phe Asp Lys Leu Glu Asp Leu Asn Lys Gly Ile Asn Glu 430        440        450        460        470        480
TTAATGAAGGTTGTAGGTGACGGTGGTATTTACATTGAGGATGTGAGAAATCTCCGGTAC
Leu Met Lys Val Val Gly Asp Gly Gly Ile Tyr Ile Glu Asp Val Arg Asn Leu Arg Tyr 490        500        510        520        530        540
GAGAACTTCGACGTACACCTTAGGAACGATGCCGGCCTGATGAAGAACTATGGCCTGCTG
Glu Asn Phe Asp Val His Leu Arg Asn Asp Ala Gly Leu Met Lys Asn Tyr Gly Leu Leu 550        560        570        580        590        600
GCTTGCTTTAAGAAAGACATGCACAAAGTGGAGACCTACCTGAAAGTCACAAAGTGCAGG
Ala Cys Phe Lys Lys Asp Met His Lys Val Glu Thr Tyr Leu Lys Val Thr Lys Cys Arg 610        620        630
CGCTTTGTAGAAAGCAACTGCACCCTGTAG
Arg Phe Val Glu Ser Asn Cys Thr Leu ***
```

*Escherichia coli* containing pEGH15 was deposited with the Fermentation Research Institute, Agency of Industrial Science and Technology, Ibarakiken, Japan as *Escherichia coli* EEGH15 (FERM BP-824) on July 2, 1985.

EXAMPLE 6

Construction of recombinant plasmid pUPA1 coding for *Anguilla japonica* growth hormone (GH-I):

In this example, 3 μg of plasmid pEGH15 containing a DNA coding for *Anguilla japonica* growth hormone was dissolved in 30 μl of a solution consisting of 10 mM Tris-HCl (pH 7.5), 7 mM MgCl₂ and 100 mM NaCl (referred to as Y-100 buffer solution hereinafter). Then, 8 units of restriction enzyme BanII (product of Toyobo Co.) and 8 units of restriction enzyme BamHI (product of Toyobo Co.) were added and digestion reaction was carried out at 37° C. for 2 hours. About 0.1 μg of a DNA fragment of about 850 bp containing the translational region of the mature growth hormone of *Anguilla japonica*, 3'-non-translational region and the vector part encoded by pEGH15 was obtained from the reaction solution by LGT method.

Separately, 2 μg of pGLM1 was dissolved in 30 μl of Y-100 buffer solution. Eight units of restriction enzyme BanIII (product of Toyobo Co.) and 8 units of restriction enzyme BamHI were added and digestion reaction was carried out at 37° C. for 2 hours. About 1.0 μg of a DNA fragment of about 4.0 Kb containing PL promoter and cI857 gene was obtained from the reaction solution by LGT method.

In order to add a translational initiation codon ATG necessary for the expression of the DNA coding for the mature growth hormone of *Anguilla japonica* and to ligate a vector DNA and the DNA mentioned above, a DNA linker set forth below was synthesized.

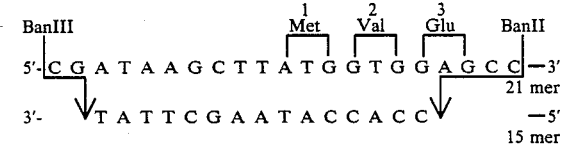

Two single stranded DNAs of 21 mer and 15 mer were synthesized by a conventional triester method [R. Crea, et al.: Proc. Natl. Acad. Sci., USA, 75, 5765 (1978)]. Then, 30 pmoles each of the 21 mer and 15 mer DNAs were dissolved in 30 μl of a solution consisting of 50 mM Tris-HCl (pH 7.5), 10 mM MgCl₂, 10 mM DTT, and 1 mM ATP. Three units of T4 polynucleotide kinase (product of Takara Shuzo Co.) were added and phosphorylation reaction was carried out at 37° C. for 40 minutes.

Then, 0.03 pmole of the BanII-BamHI fragment (about 850 bp) of pEGH15 and 0.006 pmole of the BamHI-BanIII fragment (about 4.0 Kb) of pGLM1 obtained above were dissolved in 30 μl of a solution consisting of 50 mM Tris-HCl (pH 7.5), 10 mM MgCl$_2$, 10 mM DTT and 1 mM ATP. One μl of the synthetic DNA phosphorylation reaction solution obtained above was added. Three units of T4 DNA ligase (product of Takara Shuzo Co.) was added to the mixture and ligation reaction was carried out at 4° C. for 18 hours.

*Escherichia coli* K294 (FERM BP-526 which was deposited with the FRI on Apr. 19, 1984) was transformed using the reaction solution to obtain an Ap$^R$ colony. A plasmid DNA pUPA1 illustrated in FIG. 9 was recovered from the colony. The structure of pUPA1 was recognized by the cleavage with EcoRI, BanIII, HindIII, BanII, HpaI, BamHI, BglII, PstI and XhoI and agarose gel electrophoresis.

EXAMPLE 7

Production of growth hormone polypeptide of *Anguilla japonica* (GH-I) by *Escherichia coli* containing pUPA1:

*Escherichia coli* C600 strain was transformed with the recombinant plasmid pUPA1 obtained in Example 6 by a conventional method. An Ap$^R$ colony obtained was inoculated in 10 ml pf MCG medium (pH 7.2) consisting of 0.6% Na$_2$HPO$_4$, 0.3% KH$_2$PO$_4$, 0.5% NaCl, 0.1% NH$_4$Cl, 0.5% glucose, 0.5% casamino acid, 1 mM MgSO$_4$ and 4 μg/ml vitamine B1 and culturing was carried out at 30° C. for 7 hours. The obtained culture broth was inoculated in 50 ml of MCG medium and culturing was carried out at 30° C. for 18 hours. The obtained culture broth was inoculated in one l of MCG medium and culturing was carried out at 30° C. for 5 hours, at 42° C. for 2 hours and further at 37° C. for 41 hours, respectively. The obtained culture broth was centrifuged at 8,000 rpm for 10 minutes to harvest microbial cells. The cells were suspended in Sample buffer of Laemmli and subjected to SDS-polyacrylamide gel electrophoresis and Western Blotting [Towbin, et al.: Proc. Natl. Acad. Sci., USA 76, 4350 (1979)], and thereafter by peroxidase staining method [Kazufumi Tanabe: Saibo Kogaku (Cell Engineering), 2, 1061 (1983)]to detect a polypeptide band at the portion of a molecular weight of about 26,000. The band was not observed in case of using Escherichia coli which does not contain the plasmid. As the result, it was confirmed that *Escherichia coli* carrying pUPA1 produced growth hormone polypeptide of *Anguilla japonica* in a large amount.

*Escherichia coli* containing pUPA1 was deposited with FRI as *Escherichia coli* EUPA1 under FERM BP-825 on July 2, 1980.

EXAMPLE 8

The microorganisms which produce *Anguilla japonica* growth hormone were cultured according to Example 7. The cells were collected by centrifugation at 8,000 rpm for 10 minutes and washed with a buffer solution (pH 7.5) consisting of 30 mM NaCl and 30 mM Tris-HCl. The washed cells were suspended in 5 ml of the buffer mentioned above and subjected to ultrasonic disintegration (Branson Sonic Power Company, Sonifier cell disruptor 200, output control 2, 10 minutes) 0° C. Disrupted cells were recovered by centrifugation at 15,000 rpm for 30 minutes. The disrupted cells were treated according to the method of Marston, et al. [F. A. 0. Marston, et al.: Biotechnology, 2, 800 (1984)], whereby the growth hormone polypeptide of *Anguilla japonica* was extracted, purified, solubilized and renatured. Growth promoting activity of the growth hormone polypeptide of *Anguilla japonica* was determined by the following method.

EXAMPLE 9

Construction of recombinant plasmid pUPJ24 coding for *Anguilla japonica* growth hormone (GH-II)

A recombinant plasmid coding for GH-II was constructed in the following manner.

In this step, 2 μg of recombinant plasmid pUPA1 coding for *Anguilla japonica* growth hormone (GH-I) obtained in Example 6 was dissolved in 30 μl of Y-100 buffer solution and digestion reaction was carried out with 6 units of restriction enzyme BanII (product of Toyobo Co.) at 37° C. for 2 hours. To the reaction solution, dATP and dTTP were added in a final concentration of 0.5 mM. Then, 4 units of *Escherichia coli* DNA polymerase I (product of Takara Shuzo Co.) was added and reaction was carried out at 16° C. for 30 minutes. The cohesive end formed by the digestion with BanII was changed to a flush end by the cleavage of one base of the cohesive end with the exonuclease activity of DNA polymerase I. As the result, the codon coding for isoleucine residue which is the 4th amino acid residue of GH-I was exposed at the terminal.

After phenol-chroloform extraction and ethanol precipitation, the DNA fragment was dissolved in 30 μl of Y-100 buffer solution. Digestion reaction with 6 units of restriction enzyme PstI was carried out at 37° C. for 2 hours. About 0.5 μg of a fragment of about 2.5 Kb containing the translational region of the mature growth hormone of *Anguilla japonica*, 3'-non-translational region and the *Escherichia coli* lipoprotein terminator was obtained from the reaction solution by LGT method.

Separately, 2 μg of plasmid vector pPAC1 (refer to Reference Example 1 about the construction of pPAC1) containing translational initiation codon ATG and SphI cleavage site downstream from P$_L$ promoter and ribosome binding site was dissolved in 30 μl of Y-100 buffer solution. Six units of restriction enzyme SphI (product of Boheringer Mannheim GmbH) was added and digestion reaction was carried out at 37° C. for 2 hours. To the reaction solution, dATP, dCTP, dGTP and dTTP were added in a final concentration of 0.5 mM. Then, 4 units of *Escherichia coli* DNA polymerase I·Klenow fragment (product of Takara Shuzo Co.) was added and reaction was carried out at 16° C. for 90 minutes. The 3'-cohesive end formed by the digestion with SphI was changed to a flush end by the cleavage with the 3'–5' exonuclease activity and 5'–3' repairing synthetic activity of DNA polymerase I·Klenow fragment. As the result, the translational initiation codon ATG was exposed at the terminal.

DNA polymerase I≠Klenow fragment was inactivated by heating the reaction solution at 65° C. for 20 minutes. Six units of restriction enzyme PstI was added and digestion reaction was carried out at 37° C. for 2 hours. About 0.5 μg of a fragment of about 2.2 Kb containing cI857 gene, PL promoter and the translational initiation codon ATG was obtained from the reaction solution by LGT method.

Then, 0.2 μg each of DNA fragments obtained above were dissolved in 30 μl of a solution consisting of 50 mM Tris-HCl (pH 7.5), 10 mM MgCl$_2$, 10 mM DTT and 1 mM ATP 130. 30 units of T4 DNA ligase (product of Takara Shuzo Co.) was added and ligation reaction was carried out at 4° C. for 16 hours. *Escherichia* coli K294 was transformed using the reaction solution to obtain an Ap^R colony.

Figure 10:
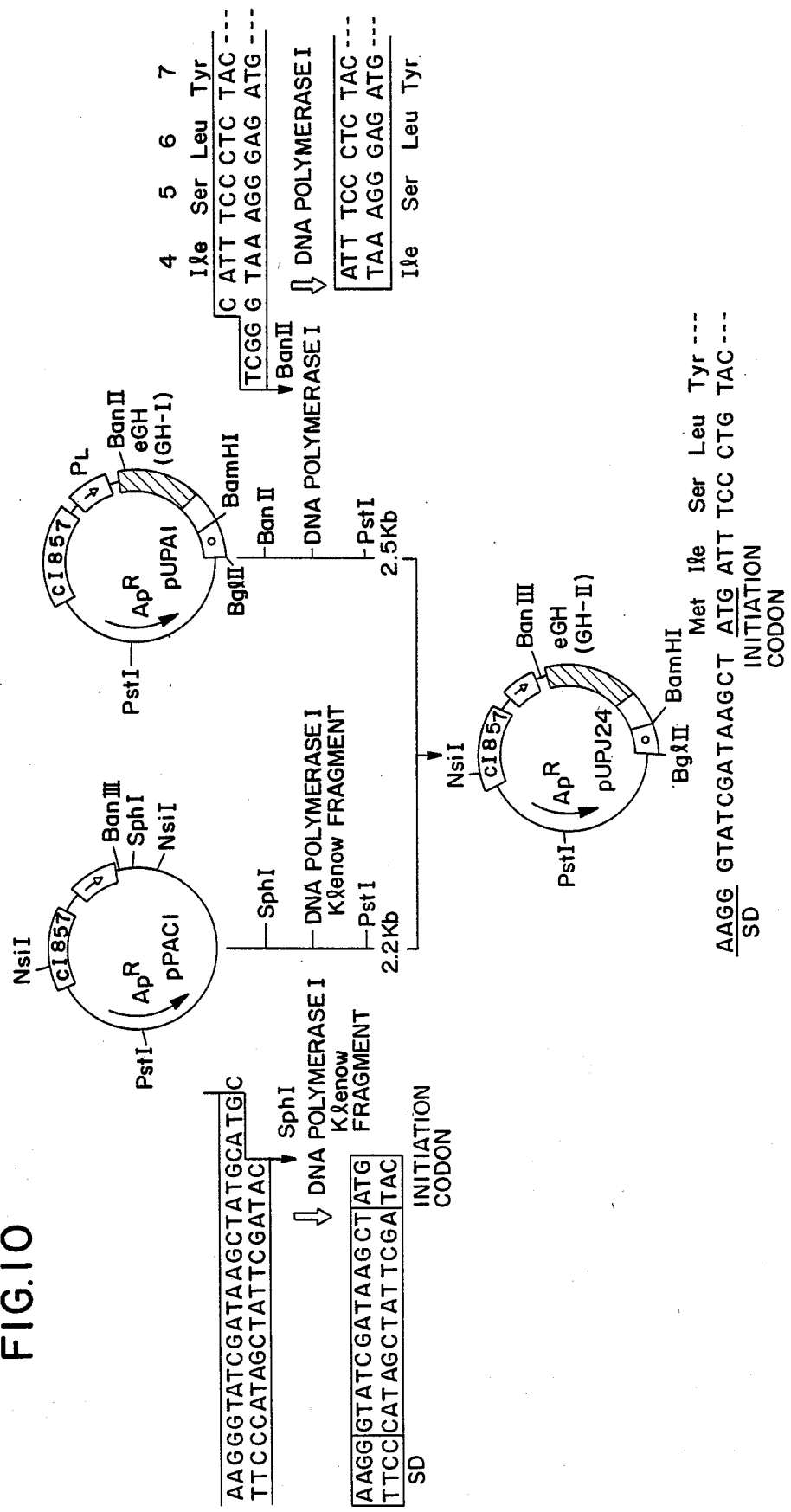
FIG. 10 illustrates the process for constructing recombinant plasmid pUPJ24.

Plasmid pUPJ24 illustrated in FIG. 10 was recovered from the colony. The structure of pUPJ24 was recognized by the cleavage with restriction enzymes PstI, BanIII, NsiI, BglII and BamHI and agarose gel electrophoresis.

It was confirmed that pUPJ24 codes for amino acid residues from the 4th to the end of GH-I in the rear of the translational initiation codon ATG, that is GH-II by the method of Sanger [Sanger, et al.; Proc. Natl. Acad. Sci., USA, 74, 5463 (1977): Amersham, M13 cloning and sequencing handbook].

EXAMPLE 10

Production of growth hormone (GH-II) polypeptide of *Anguilla japonica* by *Escherichia coli* containing pUPJ24: *Escherichia coli* K294 strain was transformed with the recombinant plasmid pUPJ24 obtained in Example 9 by a conventional method. An Ap^R colony obtained was inoculated in 5 ml of MCG medium, and culturing was carried out at 30° C. for 16 hours. Then, 100 μl of the obtained culture broth was inoculated in 5 ml of MCG medium, and culturing was carried out at 30° C. for 2 hours and at 42° C. for 2 hours, respectively. The obtained culture broth was centrifuged at 8,000 rpm for 10 minutes to recover cells. The cells were suspended in Sample buffer of Laemmli and subjected to SDS-polyacrylamide gel electrophoresis and Coomassie Brilliant Blue staining to detect a polypeptide band at the portion of a molecular weight of about 25,000. The band was not observed in the case of using *Escherichia coli* which does not contain the plasmid. Similarly, the recovered cells were suspended in Sample buffer of Laemmli and subjected to SDS-polyacrylamide gel electrophoresis, Western Blotting [Towbin, et al., Proc. Natl. staining method [Kazufumi Tanabe: Saibo Kogaku (cell Acad. Sci., USA, 76, 4350–4354 (1979)]and peroxidase Engineering), 2, 1061, (1983)]to likewise detect a polypeptide band at the portion of a molecular weight of about 25,000. The band was not observed in the case of using *Escherichia coli* which does not contain the plasmid. As the result, it was confirmed that *Escherichia coli* carrying pUPJ24 produced growth hormone polypeptide of *Anguilla japonica* in a large amount.

EXAMPLE 11

Figure 12:
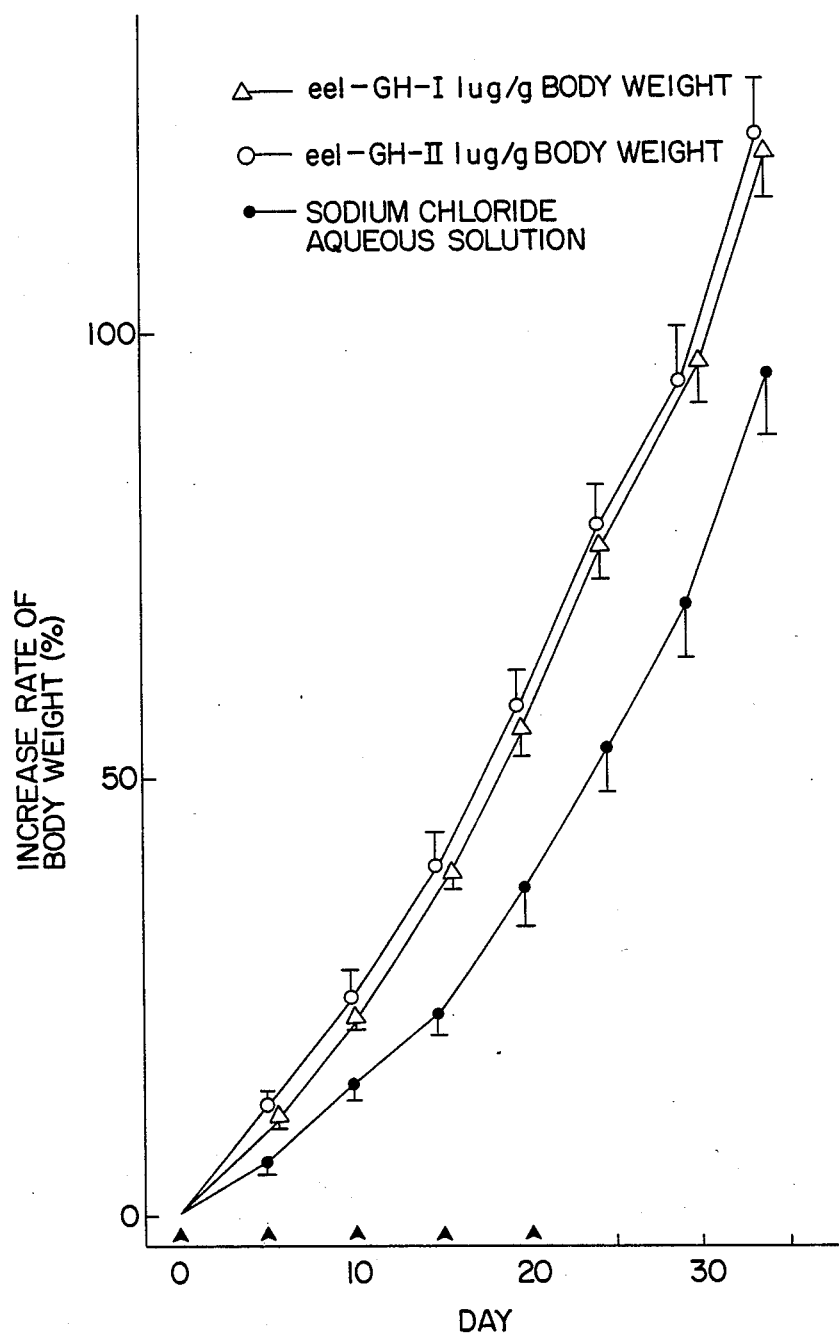
FIG. 12 illustrates how the increase in body weight of rainbow trout is promoted in administering *Anguilla japonica* growth hormone GH-I or GH-II to rainbow trout.

Determination of activity of fish growth hormones:
Fry of rainbow trout weighing an average of 13 g each were divided to groups each consisting of 15 individuals and cultivated in a cycle system tank at a water temperature of 15° C. Mixed feed (Masu 4C, product of Nippon Haigo Shiryo Co.) was given in an amount of 4% of body weight divided in two portions per day for 9 days and thereafter 3%. Growth hormones GH-I and GH-II each of *Anguilla japonica* were dissolved in a small amount of 0.01N sodium hydroxide aqueous solution and 0.9% sodium chloride aqueous solution was added to make the concentration of the growth hormones of 1 μg/5 μl. The sample solutions were injected intraperitoneally in an amount of 1 μg/g body weight. 0.9% sodium chloride aqueous solution was administered to a control group. Injection was carried out five times at an interval of five days and body weight was simultaneously measured. FIG. 12 shows increase rates of body weight. As is apparent from the results in FIG. 12, either of the growth hormones of the present invention promotes the growth of rainbow trout.

REFERENCE EXAMPLE 1

Construction of plasmid vector pPAC1 containing translational initiation codon ATG and SphI cleavage site downstream from P_L promoter and ribosome binding site pPAC1 was prepared to construct a recombinant plasmid coding for *Anguilla japonica* growth hormone (GH-II) described in the present invention.

In this step, 2 μg of plasmid vector pTrS3 (Japanese Published Unexamined Pat. Application No. 67297/84) containing translational initiation codon ATG and SphI cleavage site downstream from trp promoter and ribosome binding site was dissolved in 30 μl of Y-100 buffer solution. Four units of restriction enzyme BanIII (product of Toyobo Co.) and four units of restriction enzyme PstI were added and digestion reaction was carried out at 37° C. for 2 hours. About one μg of a DNA fragment of about 2.9 Kb containing translational initiation codon ATG and SphI cleavage site was obtained from the reaction solution by LGT method.

Figure 11:
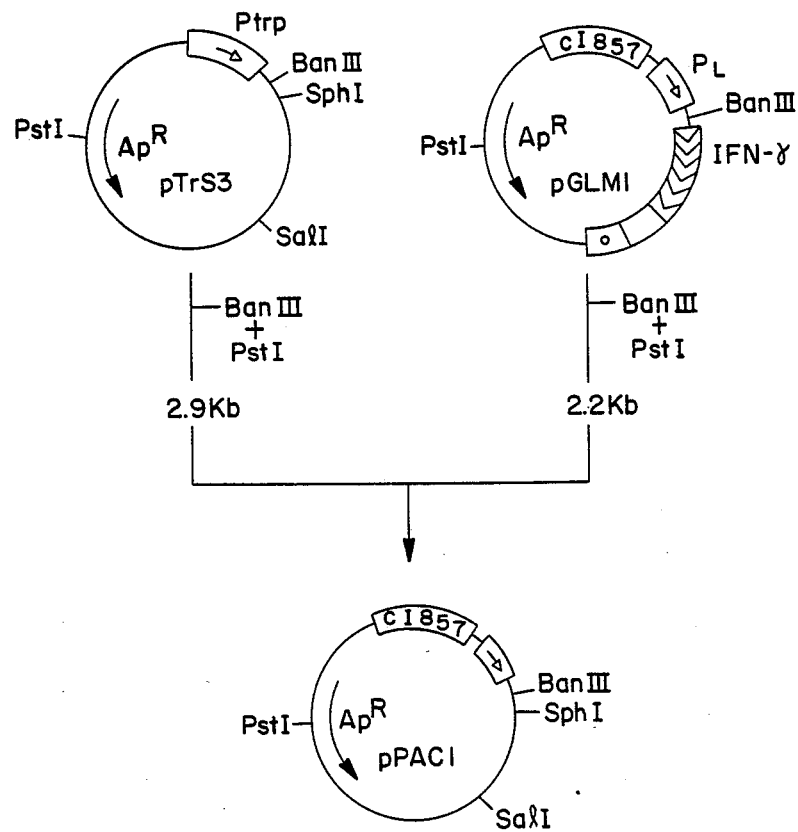
FIG. 11 illustrates the process for constructing recombinant plasmid pPAC1.

Separately, 2 μg of pGLM1 obtained from *Escherichia coli* EGLM1 (FERM BP-823) was dissolved in 30 μl of Y-100 buffer solution, and four units of restriction enzyme BanIII (product of Toyobo Co.) and 4 units of restriction enzyme PstI were added. Digestion reaction was carried out at 37° C. for 2 hours. About one μg of a DNA fragment of about 4.0 Kb containing P_L promoter and cI857 gene was obtained from the reaction solution by LGT method. Then, 0.1 μg of the DNA fragments each was dissolved in 30 μl of a solution consisting of 50 mM Tris-HCl (pH 7.5), 10 mM MgCl_2, 10 mM DTT and 1 mM ATP, and 30 units of T4 DNA ligase (product of Takara Shuzo Co.) was added. Ligation reaction was carried out at 4° C. for 16 hours. *Escherichia coli* K294 strain was transformed with the reaction solution to obtain an Ap^R colony. From the colony, plasmid pPACl as illustrated in FIG. 11 was recovered. The structure of pPACl was recognized by the cleavage with PstI, SphI, BanIII and SalI, and agarose gel electrophoresis.

What is claimed is:
1. An essentially pure fish growth hormone derived from *Anguilla japonica* which is a polypeptide having the following physicochemical properties:
 (i) Amino acid composition: as indicated in Column A, Table 1;
 (ii) The sequence of the amino acids is as follows:

H_2N—Val—Glu—Pro—Ile—Ser—Leu—Tyr—Asn—Leu—
Phe—Thr—Ser—Ala—Val—Asn—Arg—Ala—Gln—His—Leu—
His—Thr—Leu—Ala—Ala—Glu—Ile—Tyr—Lys—Glu—Phe—
Glu—Arg—Ser—Ile—Pro—Pro—Glu—Ala—His—Arg—Gln—
Leu—Ser—Lys—Thr—Ser—Pro—Leu—Ala—Gly—Cys—Tyr—
Ser—Asp—Ser—Ile—Pro—Thr—Pro—Thr—Gly—Lys—Asp—
Glu—Thr—Gln—Glu—Lys—Ser—Asp—Gly—Tyr—Leu—Leu—
Arg—Ile—Ser—Ser—Ala—Leu—Ile—Gln—Ser—Trp—Val—
Tyr—Pro—Leu—Lys—Thr—Leu—Ser—Asp—Ala—Phe—Ser—
Asn—Ser—Leu—Met—Phe—Gly—Thr—Ser—Asp—Gly—Ile—
Phe—Asp—Lys—Leu—Glu—Asp—Leu—Asn—Lys—Gly—Ile—
Asn—Glu—Leu—Met—Lys—Val—Val—Gly—Asp—Gly—Gly—
Ile—Tyr—Ile—Glu—Asp—Val—Arg—Ans—Leu—Arg—Tyr—
Glu—Asn—Phe—Asp—Val—His—Leu—Arg—Asn—Asp—Ala—
Gly—Leu—Met—Lys—Asn—Tyr—Gly—Leu—Leu—Ala—Cys—
Phe—Lys—Lys—Asp—Met—His—Lys—Val—Glu—Thr—Tyr—
Leu—Lys—Val—Thr—Lys—Cys—Arg—Arg—Phe—Val—Glu—
Ser—Asn—Cys—Thr—Leu—OH;

(iii) Molecular weight: about 23,000;

(iv) Isoelectric point: 6.3;
(v) Soluble in an alkaline aqueous solution and hardly soluble or insoluble in neutral and acidic aqueous solutions;
(vi) Classification as basic or acidic properties: acidic polypeptide;
(vii) Color and form of substance: white powder; and
(viii) Polyacrylamide gel electrophoresis: a single band.

2. An essentially pure fish growth hormone derived from *Anguilla japonica* which is a polypeptide having the following physicochemical properties:
 (i) Amino acid composition: as indicated in Column B, Table 1;
 (ii) The sequences of amino acids at the N-terminal and C-terminal are as follows:
 N-terminal:

H₂N—Ile—Ser—Leu—Tyr—Asn—Leu—Phe—Thr—Ser—
 Ala—Val—Asn—Arg—Ala—Gln—His—Leu—His—Thr—Leu—
 Ala—Ala—Glu—Ile—Tyr—Lys—Glu—Phe—Glu—Arg—Ser—
   Ile—Pro—Pro—Glu—Ala—His—Arg—Gln—Leu—

C-terminal:

—Met—Phe—Gly—Thr—Ser—Asp—Gly—Ile—Phe—Asp—
 Lys—Leu—Glu—Asp—Leu—Asn—Lys—Gly—Ile—Asn—Glu—
 Leu—Met—Lys—Val—Val—Gly—Asp—Gly—Gly—Ile—Tyr—
 Ile—Glu—Asp—Val—Arg—Asn—Leu—Arg—Tyr—Glu—Asn—
 Phe—Asp—Val—His—Leu—Arg—Asn—Asp—Ala—Gly—Leu—
 Met—Lys—Asn—Tyr—Gly—Leu—Leu—Ala—Cys—Phe—Lys—
 Lys—Asp—Met—His—Lys—Val—Glu—Thr—Tyr—Leu—Lys—
 Val—Thr—Lys—Cys—Arg—Arg—Phe—Val—Glu—Ser—Asn—

Cys—Thr—Leu—OH;

(iii) Molecular weight: about 23,000;
(iv) Isoelectric point: 6.7;
(v) Soluble in an alkaline aqueous solution and hardly soluble or insoluble in neutral and acidic aqueous solutions;

3. The fish growth hormone according to claim 1 produced by extraction from an organ culture broth of the pituitary gland of a fish belonging to *Anguilla japonica*.

4. The fish growth hormone according to claim 2 produced by extraction from an organ culture broth of the pituitary gland of a fish belonging to *Anguilla japonica*.

5. The fish growth hormone according to claim 1 which is produced by recombinant DNA techniques.

6. The fish growth hormone according to claim 2 which is produced by recombinant DNA techniques.

7. A composition comprising the fish growth hormone which is defined by claims 1, 2, 3, 4, 5 or 6 and a carrier suitable for stimulating growth of a fish.

8. A process for stimulating growth of a fish which comprises administering to the fish a growth stimulating effective amount of the fish growth hormone defined in claims 1, 2, 3, 4, 5 or 6.

9. The process according to claim 8, wherein the fish to which the fish growth hormone is administered belongs to Teleost.

10. The process according to claim 9, wherein the fish belongs to Clupeiformes, Anguilliformes, Perciformes, Pleuronectiformes or Tetraodontiformes.

* * * * *

UNITED STATES PATENT AND TRADEMARK OFFICE
CERTIFICATE OF CORRECTION

PATENT NO. : 4,894,362
DATED : January 16, 1990
INVENTOR(S) : KAZUO YAMAGUCHI

Page 1 of 3

It is certified that error appears in the above-identified patent and that said Letters Patent is hereby corrected as shown below:

COLUMN 4

Line 56, "Isoelectric point: 6.3;" should read --(iv) Isoelectric point: 6.3;--.
Line 60, "properties acidic" should read --properties: acidic--.
Line 67, "composition as" should read --composition: as--.

COLUMN 5

Line 21, "weight about" should read --weight: about--.
Line 28, "substance white" should read --substance: white--.

COLUMN 6

Line 30. "deoxynacleotidyltransferase" should read --deoxynucleotidyltransferase--.

COLUMN 12

Line 31, "Glu-Asp-Leu" should read --Glu-Asp-Leu-Asn-Lys-Gly-Ile-Asn-Glu-Leu--.

COLUMN 13

Line 67, "cut" should be deleted.

UNITED STATES PATENT AND TRADEMARK OFFICE
CERTIFICATE OF CORRECTION

PATENT NO. : 4,894,362
DATED : January 16, 1990
INVENTOR(S) : KAZUO YAMAGUCHI

Page 2 of 3

It is certified that error appears in the above-identified patent and that said Letters Patent is hereby corrected as shown below:

COLUMN 17

Table 2, "140       " should read --   140--.
         AATATA                       AATATA
Table 2, "   350" should read --   350--.
          ACTAA                    ATCAAA

COLUMN 20

Line 66, "1 mM ATP 130." should read --1 mM ATP.--.

COLUMN 21

Line 37, "Natl. staining" should read --Natl. Acad. Sci., USA, 76, 4350-4354 (1979)] and peroxidase staining--.
Line 38, "Acad. Sci., USA, 76," should be deleted.
Line 39, "4350-4354 (1979)]and peroxidase" should be deleted.

UNITED STATES PATENT AND TRADEMARK OFFICE
CERTIFICATE OF CORRECTION

PATENT NO. : 4,894,362
DATED : January 16, 1990
INVENTOR(S) : KAZUO YAMAGUCHI

It is certified that error appears in the above-identified patent and that said Letters Patent is hereby corrected as shown below:

COLUMN 24

Line 8, "solutions;" should read
--solutions;
(vi) Classification as basic or acidic properties: acidic polypeptide;
(vii) Color and form of substance: white powder; and
(viii) Polyacrylamide gel electrophoresis: a single band.--.

Signed and Sealed this

Twenty-sixth Day of February, 1991

Attest:

HARRY F. MANBECK, JR.

*Attesting Officer*  *Commissioner of Patents and Trademarks*